(12) United States Patent
Reik et al.

(10) Patent No.: US 9,957,501 B2
(45) Date of Patent: May 1, 2018

(54) NUCLEASE-MEDIATED REGULATION OF GENE EXPRESSION

(71) Applicants: Sangamo BioSciences, Inc., Richmond, CA (US); University Of Washington Through Its Center For Commercialization, Seattle, WA (US)

(72) Inventors: Andreas Reik, Richmond, CA (US); John A. Stamatoyannopoulos, Seattle, WA (US); Jeff Vierstra, Seattle, WA (US)

(73) Assignees: Sangamo Therapeutics, Inc., Richmond, CA (US); University Of Washington, Seattle, WA (US)

( * ) Notice: Subject to any disclaimer, the term of this patent is extended or adjusted under 35 U.S.C. 154(b) by 0 days. days.

(21) Appl. No.: 15/172,626

(22) Filed: Jun. 3, 2016

(65) Prior Publication Data

US 2016/0369262 A1    Dec. 22, 2016

Related U.S. Application Data

(60) Provisional application No. 62/181,583, filed on Jun. 18, 2015.

(51) Int. Cl.
| | | |
|---|---|---|
| *C12N 15/85* | (2006.01) | |
| *C12N 15/52* | (2006.01) | |
| *C12N 9/22* | (2006.01) | |
| *A61K 35/28* | (2015.01) | |
| *C12N 15/10* | (2006.01) | |
| *A61K 35/12* | (2015.01) | |
| *C07K 14/805* | (2006.01) | |

(52) U.S. Cl.
CPC ............ *C12N 15/102* (2013.01); *A61K 35/28* (2013.01); *C12N 9/22* (2013.01); *C12Y 301/00* (2013.01); *A61K 2035/124* (2013.01); *C07K 14/805* (2013.01)

(58) Field of Classification Search
None
See application file for complete search history.

(56) References Cited

U.S. PATENT DOCUMENTS

| | | |
|---|---|---|
| 5,356,802 A | 10/1994 | Chandrasegaran |
| 5,436,150 A | 7/1995 | Chandrasegaran |
| 5,487,994 A | 1/1996 | Chandrasegaran |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,081 A | 10/2000 | Barbas |
| 6,140,466 A | 10/2000 | Barbas et al. |
| 6,200,759 B1 | 3/2001 | Dove et al. |
| 6,242,568 B1 | 6/2001 | Barbas et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox et al. |
| 6,599,692 B1 | 7/2003 | Case et al. |
| 6,607,882 B1 | 8/2003 | Cox et al. |
| 6,689,558 B2 | 2/2004 | Case et al. |
| 6,794,136 B1 | 9/2004 | Eisenberg et al. |
| 6,824,978 B1 | 11/2004 | Cox et al. |
| 6,903,185 B2 | 6/2005 | Kim et al. |
| 6,933,133 B2 | 8/2005 | Case et al. |
| 6,979,539 B2 | 12/2005 | Cox et al. |
| 7,013,219 B2 | 3/2006 | Case et al. |
| 7,030,215 B2 | 4/2006 | Liu et al. |
| 7,067,317 B2 | 6/2006 | Rebar et al. |
| 7,070,934 B2 | 7/2006 | Cox et al. |
| 7,074,596 B2 | 7/2006 | Darzynkiewicz et al. |
| 7,153,949 B2 | 12/2006 | Kim et al. |
| 7,163,824 B2 | 1/2007 | Cox et al. |
| 7,253,273 B2 | 8/2007 | Collingwood |
| 7,262,054 B2 | 8/2007 | Jamieson et al. |
| 7,361,635 B2 | 4/2008 | Miller et al. |
| 7,888,121 B2 | 2/2011 | Urnov et al. |
| 7,914,796 B2 | 3/2011 | Miller et al. |
| 7,951,925 B2 | 5/2011 | Ando et al. |
| 7,972,854 B2 | 7/2011 | Miller et al. |
| 8,034,598 B2 | 10/2011 | Miller |
| 8,110,379 B2 | 2/2012 | DeKelver et al. |
| 8,153,773 B2 | 4/2012 | Jemielity et al. |
| 8,409,861 B2 | 4/2013 | Guschin et al. |
| 8,586,526 B2 | 11/2013 | Gregory et al. |
| 8,623,618 B2 | 1/2014 | Doyon et al. |
| 8,697,359 B1 | 4/2014 | Zhang |
| 8,703,489 B2 | 4/2014 | Wang |

(Continued)

FOREIGN PATENT DOCUMENTS

| | | |
|---|---|---|
| GB | 2338237 A | 12/1999 |
| WO | WO 95/19431 A1 | 7/1995 |

(Continued)

OTHER PUBLICATIONS

Bauer, et al., "An Erythroid Enhancer of BCL11Q Subject to Genetic Variation Determines Fetal Hemoglobin Level," *Science* 342(6155):253-257 (2013).
Beerli, el al., "Engineering Polydactyl Zinc-Finger Transcription Factors," *Nature Biotechnology* 20:135-141 (2002).
Chen, et al., "Developmental Silencing of Human Zeta-Globin Gene Expression Is Mediated by the Transcriptional Repressor RREB1," *J Biol Chem* 285(14):10189-10197 (2010).
Choo, et al., "Advances in Zinc Finger Engineering," *Curr. Opin. Struct. Biol.* 10:411-416 (2000).

(Continued)

*Primary Examiner* — Christopher M Babic
*Assistant Examiner* — Arthur S Leonard
(74) *Attorney, Agent, or Firm* — Dahna S. Pasternak; Pasternak Patent Law

(57) ABSTRACT

The present disclosure is in the field of genome engineering, particularly targeted modification of the genome of a hematopoietic cell.

13 Claims, 7 Drawing Sheets

(56) References Cited

U.S. PATENT DOCUMENTS

| | | | |
|---|---|---|---|
| 8,772,453 | B2 | 7/2014 | Paschon et al. |
| 8,945,868 | B2 | 2/2015 | Collingwood et al. |
| 8,956,828 | B2 | 2/2015 | Bonini et al. |
| 9,005,973 | B2 | 4/2015 | Cost et al. |
| 9,045,763 | B2 | 6/2015 | DeKelver et al. |
| 9,150,847 | B2 | 10/2015 | Rebar |
| 9,200,266 | B2 | 12/2015 | Wang |
| 9,255,250 | B2 | 2/2016 | Gregory et al. |
| 2003/0232410 | A1 | 12/2003 | Liljedahl et al. |
| 2005/0026157 | A1 | 2/2005 | Baltimore et al. |
| 2005/0064474 | A1 | 3/2005 | Urnov et al. |
| 2005/0208489 | A1 | 9/2005 | Carroll et al. |
| 2005/0267061 | A1 | 12/2005 | Martin |
| 2006/0063231 | A1 | 3/2006 | Li et al. |
| 2006/0188987 | A1 | 8/2006 | Guschan et al. |
| 2007/0218528 | A1 | 9/2007 | Miller et al. |
| 2008/0131962 | A1 | 6/2008 | Miller |
| 2008/0159996 | A1 | 7/2008 | Ando et al. |
| 2008/0299580 | A1 | 12/2008 | DeKelver et al. |
| 2009/0305419 | A1 | 12/2009 | Miller |
| 2010/0047805 | A1 | 2/2010 | Wang |
| 2010/0218264 | A1 | 8/2010 | Cui et al. |
| 2011/0182867 | A1 | 7/2011 | Orkin et al. |
| 2011/0201055 | A1 | 8/2011 | Doyon et al. |
| 2011/0207221 | A1 | 8/2011 | Cost et al. |
| 2011/0265198 | A1 | 10/2011 | Gregory et al. |
| 2011/0301073 | A1 | 12/2011 | Gregory et al. |
| 2012/0017290 | A1 | 1/2012 | Cui et al. |
| 2012/0195936 | A1 | 8/2012 | Rudolph et al. |
| 2013/0122591 | A1 | 5/2013 | Cost et al. |
| 2013/0137104 | A1 | 5/2013 | Cost et al. |
| 2013/0177983 | A1 | 7/2013 | Rebar |
| 2013/0196373 | A1 | 8/2013 | Gregory et al. |
| 2014/0093913 | A1 | 4/2014 | Cost et al. |
| 2015/0056705 | A1 | 2/2015 | Conway et al. |
| 2015/0064789 | A1 | 3/2015 | Paschon et al. |
| 2015/0132269 | A1 | 5/2015 | Orkin et al. |
| 2015/0159172 | A1 | 6/2015 | Miller et al. |
| 2015/0335708 | A1 | 11/2015 | Froelich et al. |

FOREIGN PATENT DOCUMENTS

| | | | |
|---|---|---|---|
| WO | WO 96/06166 A1 | 2/1996 | |
| WO | WO 98/37186 A1 | 8/1998 | |
| WO | WO 98/53057 A1 | 11/1998 | |
| WO | WO 98/53058 A1 | 11/1998 | |
| WO | WO 98/53059 A1 | 11/1998 | |
| WO | WO 98/53060 A1 | 11/1998 | |
| WO | WO 98/54311 A1 | 12/1998 | |
| WO | WO 00/27878 A1 | 5/2000 | |
| WO | WO 01/60970 A2 | 8/2001 | |
| WO | WO 01/88197 A2 | 11/2001 | |
| WO | WO 02/016536 A1 | 2/2002 | |
| WO | WO 02/077227 A2 | 10/2002 | |
| WO | WO 02/099084 A2 | 12/2002 | |
| WO | WO 03/016496 A2 | 2/2003 | |
| WO | WO 09/042163 A2 | 4/2009 | |

OTHER PUBLICATIONS

Cong, et al., "Multiplex Genome Engineering Using CRISPR/CAS Systems," *Science* 339(6121):819-823 (2013) doi: 10.1126/science.1231143.
Constantoulakis, et al., "Alpha-Amino-N-Butyric Acid Stimulates Fetal Hemoglobin in the Adult,"*Blood* 72(6):1961-1967(1988).
DeSimone, et al. "5-Azacytidine Stimulates Fetal Hemoglobin Synthesis in Anemic Baboons," *Proc. Natl. Aca. Sci. USA* 79:4428-4431 (1982).
Eckert, et al., "The AP-2 Family of Transcription Factors," *Genome Biology* 6:246 (2005).
Esvelt, et al., "Orthogonal Cas9 Proteins for RNA-Guided Gene Regulation and Editing," *Nature Methods* 10(11):1116-1121 (2013).
Fagerlund, et al., "The Cpf1 CRISPR-Cas Protein Expands Genome-Editing Tools," *Genome Biology* 16:251 (2015).
Ponfara, et al., "Creating Highly Specific Nucleases by Fusion of Active Restriction Endonucleases and Catalytically Inactive Homing Endonucleases," *Nucleic Acids Research* 40(2):847-860 (2012).
Prampton, et al., "Influence of the v-MyB Transactivation Domain on the Oncoprotein's Transformation Specificity," *The Embo Journal* 12(4):1333-1341 (1993).
Fu, et al., "Improving CRISPR-Cas Nuclease Specificity Using Truncated Guide RNAs," *Nature Biotechnology* 32(3):279-284 (2014).
Haft, et al., "A Guild of 45 CRISPR-Associated (Cas) Protein Families and Multiple CRISPR/Cas Subtypes Exist in Prokaryotic Genomes," *PLoS Computational Biology* 1(6):e60 (2005).
Hsu, et al., "DNA Targeting Specificity of RNA-Guided Cas9 Nucleases," *Nature Biotechnology* 31(9):827-832 (2013).
Hwang, et al., "Efficient In Vivo Genome Editing Using RNA-Guided Nucleases," *Nature Biotechnology* 31(3):227-229 (2013).
Isalan et al., "A Rapid, Generally Applicable Method to Engineer Zinc Fingers Illustrated by Targeting the HIV-1 Promoter," *Nat Biotechnol* 19:656-660 (2001).
Jansen, et al., "Identification of Genes That Are Associated With DNA Repeats in Prokaryotes," *Molecular Microbiology* 43(6):1565-1575 (2002).
Jinek, et al., "A Programmable Dual-RNA-Guided DNA Endonuclease in Adaptive Bacterial Immunity," *Science* 337:816-821 (2012).
Kariko, et al., "Incorporation of Pseudouridine into mRNA Yields Superior Nonimmunogenic Vector with Increased Translational Capacity and Biological Stability," *Molecular Therapy* 16(11):1833-1840 (2008).
Kassouf, et al., "Genome-Wide Identification of TAL1's Functional Targets: Insights Into Its Mechanisms of Action in Primary Erythroid Cells," *Genome Research* 20:1064 (2010).
Kim, et al., "Chimeric Restriction Endonuclease," *Proc. Natl. Acad. Sci. USA* 91:883-887 (1994).
Kim, et al., "Insertion and Deletion Mutants of FOKI Restriction Endonuclease,"*J. Biol. Chem.* 269(50):31978-31981 (1994).
Kormann, et al., "Expression of Therapeutic Proteins After Delivery of Chemically Modified mRNA in Mice," *Nature Biotechnology* 29(2):154-157 (2011).
Lei, et al., "Repurposing CRISPR as an RNA-Guided Platform for Sequence-Specific Control of Gene Expression," *Cell* 152(5):1173-1183 (2013).
Ley, et al., "5-Azacytidine Selectively Increases γ-Globin Synthesis in a Patient With β+ Thalassemia," *The New England Journal of Medicine* 307(24):1469-1475 (1982).
Ley, et al., "5-Azacytidine Increases Gamma-Globin Synthesis and Reduces the Proportion of Dense Cells in Patients With Sickle Cell Anemia," *Blood* 62:370-380 (1983).
Lin, et al., "Coup D'Etat: An Orphan Takes Control," *Endocrine Reviews* 32(3):404-421 (2011).
Makarova, et al., "A DNA Repair System Specific for Thermophilic Archaea and Bacteria Predicted by Genomic Context Analysis," *Nucleic Acids Res.* 30:482-496 (2002).
Makarova, et al., "A Putative RNA-Interference-Based Immune System in Prokaryotes: Computational Analysis of the Predicted Enzymatic Machinery, Functional Analogies with Eukaryotic RNAI, and Hypothetical Mechanisms of Action," *Biol. Direct* 1:7 (2006).
Maston, et al., "Transcriptional Regulatory Elements in the Human Genome," *Annual Review of Genomics and Human Genetics* 7:29-59 (2006).
McCaffrey, et al., "CRISPR-CAS9 D10A Nickase Target-Specific Fluorescent Labeling of Double Strand DNA for Whole Genome Mapping and Structural Variation Analysis," *Nucleic Acids Research* 44(2):e11 (2016) doi: 10.1093/nar/gkv878. ePub Oct. 19, 2015.
Miller, et al., "A Tale Nuclease Architecture for Efficient Genome Editing," *Nature Biotechnology* 29(2):143-148 (2011).
Neph, et al., "An Expansive Human Regulatory Lexicon Encoded in Transcription Factor Footprints," *Nature* 489:83-90 (2012).
Nishimasu, et al., "Crystal Structure of Cas9 in Complex With Guide RNA and Target DNA," *Cell* 156(5):935-949 (2014).

(56) References Cited

OTHER PUBLICATIONS

Olovnikov, et al., "Bacterial Argonaute Samples the Transcriptiome to Identify Foreign DNA," *Molecular Cell* 51:594-605 (2013).
Pabo, et al., "Design and Selection of Novel CYS2-HIS2 Zinc Finger Proteins," *Ann. Rev. Biochem.* 70:313-340 (2001).
Qin, et al., "The Critical Roles of OCUP-TFII in Tumor Progression and Metastatis," *Cell & Bioscience* 4:58 (2014).
Ran, et al., "In Vivo Genome Editing Using *Staphylococcus aureus* Cas9," *Nature* 520:186 (2015).
Sander, et al., "CRISPR-Cas Systems For Genome Editing, Regulation and Targeting," *Nature Biotechnology* 32(4):347-355 (2014).
Sankaran, et al., "Human Fetal Hemoglobin Expression is Regulated by Developmental Stage-Specific Repressor BCLIIA," *Science* 322:1839-1842 (2008).
Segal, et al., "Custom DNA-Binding Proteins Come of Age: Polydactyl Zinc-Finger Proteins," *Curr. Opin. Biotechnol.* 12:632-637 (2001).
Sheng, et al., "Structure-Based Cleavage Mechanism of *Thermus thermophilus* Argonaute DNA Guide Strand-Mediated DNA Target Cleavage," *Proc. Natl. Aca. Sci. U.S.A.* 111(2):652-657 (2014).
Shivdasani, et al., "Absence of Blood Formation in Mice Lacking the T-Cell Leukaemia Oncoprotein tal-1/SCL," *Nature* 373:432-434 (1995).
Swarts, et al., "DNA-Guided DNA Interference By a Prokaryotic Argonaute" *Nature* 507(7491):258-261 (2014).
Tebas, et al., "Gene Editing of CCR5 in Autologous CD4 T Cells of Persons Infected with HIV," *The New England Journal of Medicine* 370(10):901 (2014).
Thein, et al., "Control of Fetal Hemoglobin: New Insights Emerging from Genomics and Clinical Implications," *Human Molecular Genetics* 18(R2):R21-R223 (2009).
Thiagalingam, et al., "RREB-1, A Novel Zinc Finger Protein, Is Involved in the Differentiation Response to Ras in Human Medullary Thyroid Carcinomas" *Molecular and Cellular Biology* 16(10):5335-5345 (1996).
Vogel, "A Bacterial Seek-and-Destroy System for Foreign DNA," *Science* 344(6187):972-973 (2014).
Wadman, et al., "The LIM-Only Protein Lmo2 is a Bridging Molecule Assembling an Erythroid, DNA-Binding Complex Which Includes the TAL1, E47, GATA-1 and LDB1/NL1 Proteins," *The EMBO Journal* 16(11):3145-3157 (1997).
Wu, et al., "Dynamic Shifts in Occupancy by TAL1 are Guided by GATA Factors and Drive Large-Scale Reprogramming of Gene Expression During Hematopoiesis," *Genome Research* 24(12):1945-1962 (2014).
Wu, et al., "Genome-Wide Binding of the CRISPR Edonuclease Cas9 in Mammalian Cells," *Nature Biotechnology* (2014) doi:10.1038/nbt2889.
Xie, et al., (2005) "Systematic Discovery of Regulatory Motifs in Human Promoters and 3' UTRs by Comparison of Several Mammals," *Nature* 434(7031):338-345 (2005).
Yuan, et al., "Crystal Structure of *A. aeolicus* Argonaute, A Site-Specific DNA-Guided Endoribonuclease, Provides Insight Into RISC-Mediated mRNA Cleavage," *Molecular Cell* 19:405-419 (2005).
Zheng, et al., "GATA Transcription Factors and Cancer," *Genes & Cancer* 1(12):1178-1188 (2011).

5' CHR2 60,723,006

[AP2] [FP8]
ATCGGTGGGCCGTTTGCCCAGGGGCCTCTTTCGGAAGG
CTCTCTTGGTGATGGAGAATTGGATTTTATTTCTCAATG
GGAATGAAATAATTTGTATGCCATGCCCGTGTGGACTCCC
AAAATTGTAAAGGAGGTGAAGCTTCCCCTGTCTGCACTC
TCCCTCCCTCATAATTGTCCATTTTTCATCTGTCGGGCT
GTCC (SEQ ID NO:70)

FIGURE 1C

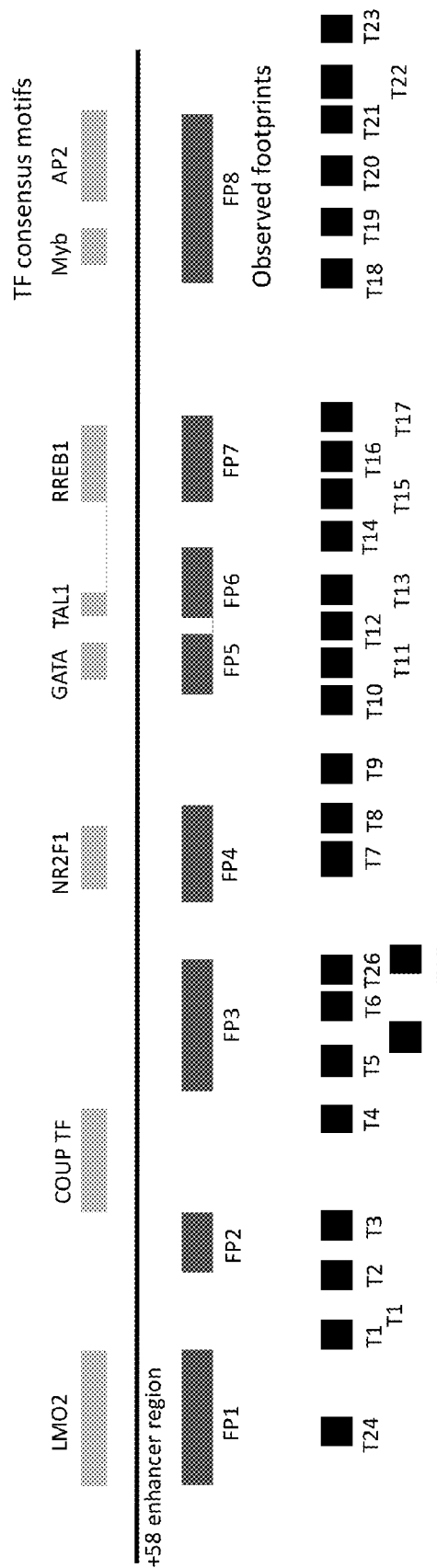

SEQUENCE LISTING

<160> NUMBER OF SEQ ID NOS: 77

<210> SEQ ID NO 1
<211> LENGTH: 18
<212> TYPE: DNA
<213> ORGANISM: Unknown
<220> FEATURE:
<223> OTHER INFORMATION: Description of Unknown:
      GATA1:TAL1 binding motif
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (8)..(15)
<223> OTHER INFORMATION: a, c, t, g, unknown or other

<400> SEQUENCE: 1
nytatcwnnn nnnnncas                                              18

<210> SEQ ID NO 2
<211> LENGTH: 9
<212> TYPE: DNA
<213> ORGANISM: Unknown
<220> FEATURE:
<223> OTHER INFORMATION: Description of Unknown:
      DNA binding motif

<400> SEQUENCE: 2 yaactgycw                                                         9

<210> SEQ ID NO 3
<211> LENGTH: 18
<212> TYPE: DNA
<213> ORGANISM: Unknown
<220> FEATURE:
<223> OTHER INFORMATION: Description of Unknown:
      DNA binding motif
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (8)..(15)
<223> OTHER INFORMATION: a, c, t, g, unknown or other

<400> SEQUENCE: 3
nytatcwnnn nnnnncas                                              18

<210> SEQ ID NO 4
<211> LENGTH: 16
<212> TYPE: DNA
<213> ORGANISM: Homo sapiens

<400> SEQUENCE: 4
tgccccaggt gtgcat                                                16

<210> SEQ ID NO 5
<211> LENGTH: 15
<212> TYPE: DNA
<213> ORGANISM: Homo sapiens

<400> SEQUENCE: 5
cagtgcaaag tccat                                                 15

<210> SEQ ID NO 6

```
<211> LENGTH: 26
<212> TYPE: DNA
<213> ORGANISM: Homo sapiens

<400> SEQUENCE: 6
ggccagaaaa gagatatggc atctac                                        26

<210> SEQ ID NO 7
<211> LENGTH: 21
<212> TYPE: DNA
<213> ORGANISM: Homo sapiens

<400> SEQUENCE: 7
acacaccagg gtcaatacaa c                                             21

<210> SEQ ID NO 8
<211> LENGTH: 15
<212> TYPE: DNA
<213> ORGANISM: Homo sapiens

<400> SEQUENCE: 8
acagttgctt ttatc                                                    15

<210> SEQ ID NO 9
<211> LENGTH: 18
<212> TYPE: DNA
<213> ORGANISM: Homo sapiens

<400> SEQUENCE: 9
ctccaggaag ggtttggc                                                 18

<210> SEQ ID NO 10
<211> LENGTH: 22
<212> TYPE: DNA
<213> ORGANISM: Homo sapiens

<400> SEQUENCE: 10
agggtggggg cgtgggtggg gt                                            22

<210> SEQ ID NO 11
<211> LENGTH: 37
<212> TYPE: DNA
<213> ORGANISM: Homo sapiens

<400> SEQUENCE: 11
tctccatcgg tggccgtttg cccagggggg cctcttt                            37

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gtgtgcataa gtaagagcag a                                             21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 13
ctgtatggac tttgcactgg a                                           21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gtaagagcag atagctgatt c                                           21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
atgttattac ctgtatggac t                                           21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
atagctgatt ccagtgcaaa g                                           21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ttttctggcc tatgttatta c                                           21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gtgcaaagtc catacaggta a                                           21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
atgccatatc tcttttctgg c                                              21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
atacaggtaa taacataggc c                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ctaagagtag atgccatatc t                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ataacatagg ccagaaaaga g                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gtgttatgtc taagagtaga t                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ctcttagaca taacacacca g                                              21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ctagactagc ttcaaagttg t                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ataacacacc agggtcaata c                                              21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gttagcttgc actagactag c                                              21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gtcaatacaa ctttgaagct a                                              21

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ataaaagcaa ctgttagctt                                                20

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ttgaagctag tctagtgcaa g                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ctggagcctg tgataaaagc a                                              21

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ctagtctagt gcaagctaac                                                20

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
cttcctggag cctgtgataa a                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gtgcaagcta acagttgctt t                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
atcagaggcc aaaccttcc t                                               21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ctaacagttg cttttatcac a                                              21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ctaatcagag gccaaaccct t                                              21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
atcacaggct ccaggaaggg t                                                 21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ctaccccacc cacgccccca c                                                 21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ctccaggaag ggtttggcct c                                                 21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ctaccccacc cacgccccca c                                                 21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ttggcctctg attagggtgg g                                                 21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ctgccagtcc tcttctaccc c                                                 21

```
<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
attagggtgg gggcgtgggt g                                                 21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
atggagaggt ctgccagtcc t                                                 21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gtggggtaga agaggactgg c                                                 21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ctgggcaaac ggccaccgat g                                                 21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ctggcagacc tctccatcgg t                                                 21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cttccgaaag aggcccccct g                                                 21
```

```
<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
atcggtggcc gtttgcccag                                                   20

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
atcaccaaga gagccttccg a                                                 21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gtttgcccag gggggcctct t                                                 21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
attctccatc accaagagag c                                                 21

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ttgcccaggg gggcctcttt c                                                 21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ataaaatcca attctccatc a                                                 21

<210> SEQ ID NO 56
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ctttcggaag gctctcttgg t                                              21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
attgagaaat aaaatccaat t                                              21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
atacagggct ggctctatgc c                                              21

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ctatctgctc ttacttatgc                                                20

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gtaataacat aggccagaaa a                                              21

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gttatgtcta agagtagatg c                                              21

<210> SEQ ID NO 62
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ataggccaga aaagagatat g                                              21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ctggtgtgtt atgtctaaga g                                              21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
ataggccaga aaagagatat g                                              21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
attgaccctg gtgtgttatg t                                              21

<210> SEQ ID NO 66

<400> SEQUENCE: 66

000

<210> SEQ ID NO 67

<400> SEQUENCE: 67

000

<210> SEQ ID NO 68
<211> LENGTH: 174
<212> TYPE: DNA
<213> ORGANISM: Homo sapiens

<400> SEQUENCE: 68
gaggtactga tggaccttgg gtgctattcc tgtgataagg aaggcagcta gacaggactt    60
gggagttatc tgtagtgaga tggctgaaaa gcgatacagg gctggctcta tgccccaggt   120
gtgcataagt aagagcagat agctgattcc agtgcaaagt ccatacaggt aata         174

<210> SEQ ID NO 69
```

<211> LENGTH: 180
<212> TYPE: DNA
<213> ORGANISM: Homo sapiens

<400> SEQUENCE: 69

```
acataggcca gaaaagagat atggcatcta ctcttagaca taacacacca gggtcaatac    60
aactttgaag ctagtctagt gcaagctaac agttgctttt atcacaggct ccaggaaggg   120
tttggcctct gattagggtg ggggcgtggg tggggtagaa gaggactggc agacctctcc   180
```

<210> SEQ ID NO 70
<211> LENGTH: 199
<212> TYPE: DNA
<213> ORGANISM: Homo sapiens

<400> SEQUENCE: 70

```
atcggtggcc gtttgcccag gggggcctct ttcggaaggc tctcttggtg atggagaatt    60
ggatttattt tctcaatggg aatgaaataa tttgtatgcc atgccgtgtg gactcccaaa   120
attgtaaagg aggtgaagct tccctgtct gcactctccc ctcctcataa ttgtccattt    180
ttcatctgtc gggctgtcc                                                 199
```

<210> SEQ ID NO 71
<211> LENGTH: 60
<212> TYPE: DNA
<213> ORGANISM: Homo sapiens

<400> SEQUENCE: 71

```
gcaagctaac agttgctttt atcacaggct ccaggaaggg tttggcctct gattagggtg    60
```

<210> SEQ ID NO 72
<211> LENGTH: 60
<212> TYPE: DNA
<213> ORGANISM: Homo sapiens

<400> SEQUENCE: 72

```
gcaagctaac agttgctttt atcacaggct ccaggaaggg tttggcctct gattagggtg    60
```

<210> SEQ ID NO 73
<211> LENGTH: 60
<212> TYPE: DNA
<213> ORGANISM: Homo sapiens

<400> SEQUENCE: 73

```
tttggcctct gattagggtg ggggcgtggg tggggtagaa gaggactggc agacctctcc    60
```

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74

```
ttgcttttat cacaggctcc                                                20
```

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 75
attagggtgg gggcgtgggt                                              20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
ttagggtggg ggcgtgggtg                                              20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
tctgattagg gtgggggcgt                                              20
```

NUCLEASE-MEDIATED REGULATION OF GENE EXPRESSION

CROSS-REFERENCE TO RELATED APPLICATIONS

The present application claims the benefit of U.S. Provisional Application 62/181,583, filed Jun. 18, 2015, the disclosure of which is hereby incorporated by reference in its entirety herein.

SEQUENCE LISTING

The instant application contains a Sequence Listing which has been submitted electronically in ASCII format and is hereby incorporated by reference in its entirety. Said ASCII copy, created on Jul. 8, 2016, is named 8328-0137$_{13}$SL.txt and is 17,535 bytes in size.

TECHNICAL FIELD

The present disclosure is in the field of genome engineering, particularly targeted modification of the genome of a hematopoietic cell.

BACKGROUND

When one considers that genome sequencing efforts have revealed that the human genome contains between 20,000 and 25,000 genes, but fewer than 2000 transcriptional regulators, it becomes clear that a number of factors must interact to control gene expression in all its various temporal, developmental and tissue specific manifestations. Expression of genes is controlled by a highly complex mixture of general and specific transcriptional regulators and expression can also be controlled by cis-acting DNA elements. These DNA elements comprise both local DNA elements such as the core promoter and its associated transcription factor binding sites as well as distal elements such as enhancers, silencers, insulators and locus control regions (LCRs) (see Maston et al (2006) *Ann Rev Genome Hum Genet* 7:29-50).

Enhancer elements were first identified in the SV40 viral genome, and then found in the human immunoglobulin heavy chain locus. Now known to play regulatory roles in the expression of many genes, enhancers appear to mainly influence temporal and spatial patterns of gene expression. It has also been found that enhancers function in a manner that is not dependent upon distance from the core promoter of a gene, and is not dependent on any specific sequence orientation with respect to the promoter. Enhancers can be located several hundred kilobases upstream or downstream of a core promoter region, where they can be located in an intron sequence, or even beyond the 3' end of a gene.

Various methods and compositions for targeted cleavage of genomic DNA have been described. Such targeted cleavage events can be used, for example, to induce targeted mutagenesis, induce targeted deletions of cellular DNA sequences, and facilitate targeted recombination at a predetermined chromosomal locus. See, e.g., U.S. Pat. Nos. 9,255,250; 9,200,266; 9,045,763; 9,005,973; 9,150,847; 8,956,828; 8,945,868; 8,703,489; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publications 20030232410; 20050208489; 20050026157; 20050064474; 20060063231; 20080159996; 20100218264; 20120017290; 20110265198; 20130137104; 20130122591; 20130177983; 20130196373; 20140093913; 20150056705; 20150335708; and 20150132269, the disclosures of which are incorporated by reference in their entireties for all purposes. These methods often involve the use of engineered cleavage systems to induce a double strand break (DSB) or a nick in a target DNA sequence such that repair of the break by an error born process such as non-homologous end joining (NHEJ) or repair using a repair template (homology directed repair or HDR) can result in the knock out of a gene or the insertion of a sequence of interest (targeted integration). This technique can also be used to introduce site specific changes in the genome sequence through use of a donor oligonucleotide, including the introduction of specific deletions of genomic regions, or of specific point mutations or localized alterations (also known as gene correction). Cleavage can occur through the use of specific nucleases such as engineered zinc finger nucleases (ZFN), transcription-activator like effector nucleases (TALENs), or using a CRISPR/Cas system (including Cfp1) with an engineered crRNA/tracr RNA ('single guide RNA') to guide specific cleavage. Further, targeted nucleases are being developed based on the Argonaute system (e.g., from *T. thermophilus*, known as 'TtAgo', see Swarts et al (2014) *Nature* 507(7491): 258-261), which also may have the potential for uses in genome editing and gene therapy.

Red blood cells (RBCs), or erythrocytes, are the major cellular component of blood. In fact, RBCs account for one quarter of the cells in a human. Mature RBCs lack a nucleus and many other organelles in humans, and are full of hemoglobin, a metalloprotein that functions to carry oxygen to the tissues as well as carry carbon dioxide out of the tissues and back to the lungs for removal. This protein makes up approximately 97% of the dry weight of RBCs and it increases the oxygen carrying ability of blood by about seventy fold. Hemoglobin is a heterotetramer comprising two alpha (α)-like globin chains and two beta (β)-like globin chains and 4 heme groups. In adults the α2β2 tetramer is referred to as Hemoglobin A (HbA) or adult hemoglobin. Typically, the alpha and beta globin chains are synthesized in an approximate 1:1 ratio and this ratio seems to be critical in terms of hemoglobin and RBC stabilization. In a developing fetus, a different form of hemoglobin, fetal hemoglobin (HbF), is produced which has a higher binding affinity for oxygen than Hemoglobin A such that oxygen can be delivered to the baby's system via the mother's blood stream. Fetal hemoglobin also contains two α globin chains, but in place of the adult β-globin chains, it has two fetal gamma (γ)-globin chains (i.e., fetal hemoglobin is α2γ2). At approximately 30 weeks of gestation, the synthesis of gamma globin in the fetus starts to drop while the production of beta globin increases. By approximately 10 months of age, the newborn's hemoglobin is nearly all α2β2 although some HbF persists into adulthood (approximately 1-3% of total hemoglobin). The regulation of the switch from production of gamma- to beta-globin is quite complex, and primarily involves a down-regulation of gamma globin transcription with a simultaneous up-regulation of beta globin transcription.

Genetic defects in the sequences encoding the hemoglobin chains can be responsible for a number of diseases known as hemoglobinopathies, including sickle cell anemia and thalassemias. In the majority of patients with hemoglobinopathies, the genes encoding gamma globin remain present, but expression is relatively low due to normal gene repression occurring around parturition as described above.

It is estimated that 1 in 5000 people in the U.S. have sickle cell disease (SCD), mostly in people of sub-Saharan Africa descent. There appears to be a benefit for heterozygous carriers of the sickle cell mutation for protection against malaria, so this trait may have been positively selected over time, such that it is estimated that in sub-Saharan Africa, one third of the population has the sickle cell trait. Sickle cell disease is caused by a mutation in the β globin gene as a consequence of which valine is substituted for glutamic acid at amino acid #6 (a GAG to GTG at the DNA level), where the resultant hemoglobin is referred to as "hemoglobinS" or "HbS." Under lower oxygen conditions, a conformational shift in the deoxy form of HbS exposes a hydrophobic patch on the protein between the E and F helices. The hydrophobic residues of the valine at position 6 of the beta chain in hemoglobin are able to associate with the hydrophobic patch, causing HbS molecules to aggregate and form fibrous precipitates. These aggregates in turn cause the abnormality or 'sickling' of the RBCs, resulting in a loss of flexibility of the cells. The sickling RBCs are no longer able to squeeze into the capillary beds and can result in vaso-occlusive crisis in sickle cell patients. In addition, sickled RBCs are more fragile than normal RBCs, and tend towards hemolysis, eventually leading to anemia in the patient.

Treatment and management of sickle cell patients is a life-long proposition involving antibiotic treatment, pain management and transfusions during acute episodes. One approach is the use of hydroxyurea, which exerts its effects in part by increasing the production of gamma globin. Long term side effects of chronic hydroxyurea therapy are still unknown, however, and treatment gives unwanted side effects and can have variable efficacy from patient to patient. Despite an increase in the efficacy of sickle cell treatments, the life expectancy of patients is still only in the mid to late 50's and the associated morbidities of the disease have a profound impact on a patient's quality of life.

Thalassemias are also diseases relating to hemoglobin and typically involve a reduced expression of globin chains. This can occur through mutations in the regulatory regions of the genes or from a mutation in a globin coding sequence that results in reduced expression or reduced levels or functional globin protein. Alpha thalassemias are mainly associated with people of Western Africa and South Asian descent, and may confer malarial resistance. Beta thalassemia is mainly associated with people of Mediterranean descent, typically from Greece and the coastal areas of Turkey and Italy. Treatment of thalassemias usually involves blood transfusions and iron chelation therapy. Bone marrow transplants are also being used for treatment of people with severe thalassemias if an appropriate donor can be identified, but this procedure can have significant risks.

One approach that has been proposed for the treatment of both SCD and beta thalassemias is to increase the expression of gamma globin with the aim to have HbF functionally replace the aberrant adult hemoglobin. As mentioned above, treatment of SCD patients with hydroxyurea is thought to be successful in part due to its effect on increasing gamma globin expression. The first group of compounds discovered to affect gamma globin reactivation activity were cytotoxic drugs. The ability to cause de novo synthesis of gamma-globin by pharmacological manipulation was first shown using 5-azacytidine in experimental animals (DeSimone (1982) *Proc Nat'l Acad Sci USA* 79(14):4428-31). Subsequent studies confirmed the ability of 5-azacytidine to increase HbF in patients with β-thalassemia and sickle cell disease (Ley, et al., (1982) *N. Engl. J. Medicine*, 307: 1469-1475, and Ley, et al., (1983) *Blood* 62: 370-380). In addition, short chain fatty acids (e.g. butyrate and derivatives) have been shown in experimental systems to increase HbF (Constantoulakis et al., (1988) *Blood* 72(6):1961-1967). Also, there is a segment of the human population with a condition known as 'Hereditary Persistence of Fetal Hemoglobin' (HPFH) where elevated amounts of HbF persist in adulthood (10-40% in HPFH heterozygotes (see Thein et al (2009) *Hum. Mol. Genet* 18 (R2): R216-R223). This is a rare condition, but in the absence of any associated beta globin abnormalities, is not associated with any significant clinical manifestations, even when 100% of the individual's hemoglobin is HbF. When individuals that have a beta thalassemia also have co-incident HPFH, the expression of HbF can lessen the severity of the disease. Further, the severity of the natural course of sickle cell disease can vary significantly from patient to patient, and this variability, in part, can be traced to the fact that some individuals with milder disease express higher levels of HbF.

One approach to increase the expression of HbF involves identification of genes whose products play a role in the regulation of gamma globin expression. One such gene is BCL11A, first identified because of its role in lymphocyte development. BCL11A encodes a zinc finger protein that is thought to be involved in the developmental stage-specific regulation of gamma globin expression. BCL11A is expressed in adult erythroid precursor cells and down-regulation of its expression leads to an increase in gamma globin expression. In addition, it appears that the splicing of the BCL11A mRNA is developmentally regulated. In embryonic cells, it appears that the shorter BCL11A mRNA variants, known as BCL11A-S and BCL11A-XS are primary expressed, while in adult cells, the longer BCL11A-L and BCL11A-XL mRNA variants are predominantly expressed. See, Sankaran et al (2008) *Science* 322 p. 1839. The BCL11A protein appears to interact with the beta globin locus to alter its conformation and thus its expression at different developmental stages. Use of an inhibitory RNA targeted to the BCL11A gene has been proposed (see, e.g., U.S. Patent Publication 20110182867) but this technology has several potential drawbacks, namely that complete knock down may not be achieved, delivery of such RNAs may be problematic and the RNAs must be present continuously, requiring multiple treatments for life.

Targeting of BCL11A enhancer sequences provides a mechanism for increasing HbF. See, e.g., U.S. patent application Ser. No. 14/540,729. Genome wide association studies have identified a set of genetic variations at BCL11A that are associated with increased HbF levels. These variations are a collection of SNPs found in non-coding regions of BCL11A that function as a stage-specific, lineage-restricted enhancer region. Further investigation revealed that this BCL11A enhancer is required in erythroid cells for BCL11A expression, but is not required for its expression in B cells (see Bauer et al, (2013) *Science* 343:253-257). The enhancer region was found within intron 2 of the BCL11A gene, and three areas of DNAseI hypersensitivity (often indicative of a chromatin state that is associated with regulatory potential) in intron 2 were identified. These three areas were identified as "+62", "+58" and "+55" in accordance with the distance in kilobases from the transcription start site of BCL11A. These enhancer regions are roughly 350 (+55); 550 (+58); and 350 (+62) nucleotides in length (Bauer 2013, ibid).

Histone modifications were also observed in this region in primary human erythroblasts that contained SNPs associated with increased HbF expression. Additionally, it was shown that the erythroid related transcription factors GATA1 and TAL1 bind within the BCL11A intron 2 region. GATA transcription factors are zinc finger DNA binding proteins that control development in many different tissues by activating or repressing gene expression. GATA factors typically bind to the element A/T GATA A/G and were initially characterized by their involvement in the expression of erythroid-specific genes. Now several members of the GATA transcription factor family have been described that play essential roles in the expression of genes in a number of cell types (Zheng and Blobel (2011) *Genes & Cancer* 1(12):1178-1188). TAL1 is a transcription factor of the basic helix-loop-helix class. It was initially identified as activated in T cell leukemia, but then shown (Shivdasani et al (1995) *Nature* 373:432) to be essential for hematopoiesis broadly, and specifically within the context of erythropoiesis, to be required at the myelo-erythroid stage. TAL-1 is an obligate heterodimer, and genome-wide occupancy data have shown that TAL-1 and GATA-1 commonly co-occupy and co-regulate target genes during erythropoiesis (Wu et al (2014) *Gen Res* 24:1945). GATA-1/TAL-1 heterodimers typically bind to the motif NT/CTATCT/ANNNNNNNNCAG/C (SEQ ID NO:1), termed the GATA1:TAL1 binding motif (Kassouf et al (2010) *Gen Res* 20:1064).

RREB1 (Ras Responsive Element Binding protein) is a broadly expressed transcription factor that contains a C2H2 zinc finger protein DNA binding domain. It was initially identified as required for the response of specific genes to Ras signaling (Thiagalingam et al, (1996) *Mol Cell Bio* 16(10):5335). More recently, Chen et al (2010), *J Biol Chem* 285(14):10189) have discovered that the gene encoding the embryonic/fetal form of the alpha globin gene (known as zeta globin) is bound by, and is regulated, by RREB1, thus pointing to its specific function as a regulator of the fetal-to-adult globin transition during erythropoiesis. The DNA motif that RREB1 appears to bind to is GTGGGTGG/T (Xie et al (2005) *Nature* 434(7031):338).

LMO2 belongs to a subset of the large LMO family of zinc finger proteins (Wadman et al (1997) *EMBO J* 16(11): 3145). These proteins comprise two LIM DNA binding proteins and are thought to be scaffolding proteins involved in multiprotein complex formation. The LMO2 complex is an essential transcriptional regulator in hematopoiesis, whose inappropriate regulation can contribute to the development of leukemia. The complex appears to interact with the DNA in two locations: the first is at an E box motif (5'CACGTG) and the second is a nearby GATA-1 binding motif.

Transcription factor chicken ovalbumin upstream promoter transcription factor II (COUP-TF2 (also known as NR2F2)) is widely expressed during embryonic development in a number of tissues and is part of the nuclear receptor (NR) superfamily of ligand-activated receptors. It is also a zinc finger protein and is involved in activating or repressing gene expression depending on direct binding to its motif and/or interaction with other transcription factors. COUP-TF2 recognizes a DNA motif with the following sequence: 5' AGGTCA and serves as one of the master regulators to control developmental programs, including organogenesis, angiogenesis, cardiovascular development, reproduction, neuronal development and metabolic homeostasis (Qin et al (2014) *Cell Biosci* 4:58).

The transcription factor NR2F1 is closely related to COUP-TF2, sharing 97% and 99% homology in its ligand and DNA binding domains respectively. Both NR2F1 and COUP-TF2 form homodimers and bind the same DNA motif (Lin et al (2011) *Endocr Rev* 32(3):404).

C-Myb can act as a transcription factor in hematopoietic cells and can be regulated by lineage specific components (see Frampton et al (1993) *EMBO J* 12(4):1333). It interacts with the DNA binding motif 5' C/TAACTGC/TCA/T (SEQ ID NO:2).

The AP-2 family of transcription factors consists of five different proteins in humans and mice: AP-2α, AP-2β, AP-2γ, AP-2δ and AP-2ε. The proteins have a characteristic helix-span-helix motif at the carboxyl terminus, which, together with a central basic region, mediates dimerization and DNA binding. AP-2 has been shown to bind to the palindromic consensus sequence 5'-GCCN3GGC-3' found in various cellular and viral enhancers and seems to be involved with embryonic development (Eckert et al (2005) *Genome Biol* 6:246).

There remains a need for additional methods and compositions for the alteration of BCL11A gene expression for example to treat hemoglobinopathies such as sickle cell disease and beta thalassemia.

SUMMARY

The present invention describes compositions and methods for use in gene therapy and genome engineering. Specifically, the methods and compositions described relate to inactivating (e.g., by completely or partially abolishing its expression) a BCL11A gene, for example a gene that acts as regulator of one or more additional genes. In particular, the invention describes methods and compositions for interfering with enhancer function in a BCL11A gene to diminish or knock out its activity in specific cell lineages. Additionally, the invention provides methods and compositions for interfering with BCL11A enhancer functions wherein the enhancer sequences are not located within the coding portion of the BCL11A gene. The resulting down-regulation of the BCL11A gene in these circumstances in turn results in increased expression of gamma globin.

In one aspect, the invention includes a genetically modified cell comprising a genomic modification made by a nuclease, wherein the genomic modification comprises insertions and/or deletions within any of SEQ ID NOs:58-65 or 74-77. The cell may be a stem cell, for example a hematopoietic stem cell (e.g., CD34+ cell) or a genetically modified differentiated cell descended from the stem cell as described herein (e.g., a red blood cell (RBC)). In certain embodiments, the nuclease comprises at least one zinc finger nuclease (ZFN), TALEN or CRISPR/Cas nuclease (including Cfp1). The nuclease may be introduced into the cell as a polynucleotide. In certain embodiments, the insertion comprises integration of a donor polynucleotide encoding a transgene. Also provided is a pharmaceutical composition comprising one or more genetically modified cells as described herein.

In some aspects, the invention comprises a non-naturally occurring zinc finger protein comprising a zinc finger protein (ZFP) comprising 4, 5 or 6 fingers, each finger comprising a recognition helix region that recognizes a target subsite in the BCL11A enhancer region. In other aspects, the invention comprises a non-naturally occurring TALE or CRIPSR/Cas system that recognizes a target subsite in the BCL11A enhancer region. In some embodiments, the ZFP, TALE or CRISPR/Cas system comprises a functional nuclease domain such that the target subsite in the BCL11A enhancer sequence is cleaved by the nuclease domain. In other embodiments, the ZFP, TALE or CRISPR/Cas system does not comprise a functional nuclease activity but does comprise a functional DNA binding activity to interact with the target sub site. In further embodiments, the nuclease deficient DNA binding activity of a ZFP, TALE or CRISPR/

Cas system of the invention serves to block the target sub site from interacting with other DNA binding proteins. In some embodiments, the target subsite is in a BCL11A enhancer region, and binding of the nuclease deficient DNA binding protein of the invention prevents interaction with a transcription factor.

In some aspects, the target subsite is at or near a DNA binding motif for a transcription factor. In some embodiments, the DNA binding motif is recognized by the GATA-1 transcription factor, and comprises the sequence A/T GATA A/G. In other embodiments, the DNA binding motif is recognized by a GATA-1/TAL-1 heterodimer, and comprises the sequence NT/CTATCT/ANNNNNNNNCAG/C (SEQ ID NO:3). In still further embodiments, the DNA binding motif is recognized by an RREB1 transcription factor and comprises the sequence GTGGGTGG/T. In certain embodiments, described herein is a DNA binding molecule comprising a TALE-effector protein (TALE) or a single guide RNA that binds to a target site as shown in any of SEQ ID Nos:58-65 or 74-77. A polynucleotide encoding one or more DNA-binding molecules as described herein are also provided. Isolated cells comprising one or more DNA-binding molecules as described herein are also provided.

In some aspects, binding of a nuclease deficient DNA binding molecule of the invention at or near a DNA binding motif prevents or inhibits binding of a transcription factor. In some embodiments, the DNA binding motif is in a BCL11A enhancer region. In further embodiments, the transcription factor blocked by the DNA binding protein of the invention is GATA-1, a GATA-1/TAL-1 heterodimer, or RREB1. In some embodiments, expression of the BCL11A protein is prevented, inhibited or decreased by the binding of the DNA binding protein of the invention to a GATA-1, a GATA-1/TAL1 or RREB1 binding motif.

In some aspects, cleavage at the target subsite by a nuclease of the invention results in a modification at or near a DNA binding motif used by a transcription factor. In some embodiments, the DNA binding motif is recognized by GATA-1, a GATA-1/TAL-1 heterodimer or RREB1 such that the modification at or near the motif prevents or inhibits binding by the transcription factor. In some embodiments, expression of the BCL11A protein is prevented, inhibited or decreased by the modification.

In another aspect, the invention comprises delivery of at least one nuclease or DNA binding molecule (e.g., a nuclease or DNA binding molecule that binds to a target sub site within a BCL11A enhancer sequence) to a human stem cell or precursor cell (HSC/PC) for the purpose of genome engineering. In certain embodiments, the nuclease or DNA binding molecule comprises a zinc finger protein (ZFP) comprising 4, 5 or 6 fingers, each finger comprising a recognition helix region that recognizes a target subsite. In other embodiments, the nuclease or DNA binding molecule comprises a TALE comprising a DNA binding domain that recognizes a target subsite. In still further embodiments, the nuclease or DNA binding molecule comprises a CRISPR/Cas system and comprises a guide RNA that interacts with a target subsite.

In some embodiments, the nuclease is delivered as a peptide, while in others it is delivered as a nucleic acid encoding the at least one nuclease. In some embodiments, more than one nuclease is used. In some preferred embodiments, the nucleic acid encoding the nuclease is an mRNA, and in some instances, the mRNA is protected. In some aspects, the mRNA may be chemically modified (See e.g. Kormann et al, (2011) *Nature Biotechnology* 29(2):154-157). In other aspects, the mRNA may comprise an ARCA cap (see U.S. Pat. Nos. 7,074,596 and 8,153,773). In further embodiments, the mRNA may comprise a mixture of unmodified and modified nucleotides (see U.S. Patent Publication 2012/0195936). In a preferred embodiment, the nucleic acid encoding the nuclease(s) is delivered to the HSC/PC via electroporation.

In other aspects, the invention comprises a cell or cell line in which an endogenous BCL11A enhancer sequence is genetically modified by a nuclease as described herein, for example as compared to the wild-type sequence of the cell. Nuclease-modified cells or cell lines as described herein are distinguishable in structure and/or function from both wild-type and other modified (nuclease-mediated) cells. The genetically modified cell or cell lines may be heterozygous or homozygous for the modification. The modifications may comprise insertions (e.g., transgene insertion), deletions and/or combinations thereof. In some preferred embodiments, the insertions, deletions and/or combinations thereof result in the destruction of a transcription factor binding site. In certain embodiments, the modification is at or near the nuclease(s) binding and/or cleavage site(s), for example, includes nucleotides within the binding and/or cleavage site as well nucleotides 1-300 (or any value therebetween) base pairs upstream or downstream of the site(s) of binding/cleavage, more preferably within the binding and/or cleavage site(s) and/or 1-100 base pairs (or any value therebetween) of either side of the binding and/or cleavage site(s) shown in Table 1 or Table 2 (SEQ ID NO:1 to 65) and/or SEQ ID NOs:74 to 77, even more preferably within the binding and/or cleavage site(s) and/or 1 to 50 base pairs (or any value therebetween) on either side of the binding and/or cleavage site(s). In certain embodiments, the nuclease target site(s) is(are) not modified. In other embodiments, at least one of the target sites for the nuclease(s) is(are) modified (nucleotides inserted and/or deleted in the target site(s)). In certain embodiments, the modification is at or near the "+58" region of the BCL11A enhancer. Any cell or cell line may be modified by the nucleases as described herein, for example a stem cell (hematopoietic stem cell such as a CD34+ hematopoietic stem cell) or red blood cell (RBC) precursor cell. Also described are cells or cell lines obtained following modification by a nuclease as described herein, for example cells or cell lines descended from a nuclease-modified cell or cell line. Partially or fully differentiated cells descended from the modified stem cells as described herein are also provided (e.g., RBCs or RBC precursor cells). Any of the genetically modified cells or cell lines disclosed herein may show increased expression of gamma globin. Compositions such as pharmaceutical compositions comprising the genetically modified cells as described herein are also provided.

In other aspects, the invention comprises delivery of a donor nucleic acid to a target cell to provide a genetically modified cell in which the donor is integrated into the cell. The donor may be delivered prior to, after, or along with the nucleic acid encoding the nuclease(s) as described herein. The donor nucleic acid may comprise an exogenous sequence (transgene) to be integrated into the genome of the cell, for example, an endogenous locus. In some embodiments, the donor may comprise a full length gene or fragment thereof flanked by regions of homology with the targeted cleavage site. In some embodiments, the donor lacks homologous regions and is integrated into a target locus through homology independent mechanism (i.e. NHEJ). The donor may comprise any nucleic acid sequence, for example a nucleic acid that, when used as a substrate for homology-directed repair of the nuclease-induced double-strand break, leads to a donor-specified deletion to be generated at the endogenous chromosomal locus (e.g., BCL11A enhancer region) or, alternatively (or in addition to), novel allelic forms of (e.g., point mutations that ablate a transcription factor binding site) the endogenous locus to be created. In some aspects, the donor nucleic acid is an oligonucleotide wherein integration leads to a gene correction event, or a targeted deletion. In some embodiments, the donor is maintained and expressed extra-chromosomally.

In other aspects, the nuclease and/or donor is(are) delivered by viral and/or non-viral gene transfer methods. In preferred embodiments, the donor is delivered to the cell via an adeno-associated virus (AAV). In some embodiments, the AAV delivers a cDNA construct comprising a donor transgene or interest operably linked to regulatory sequences such that the cDNA construct is maintained and expressed extra-chromosomally. In some instances, the AAV comprises LTRs that are of a heterologous serotype in comparison with the capsid serotype.

In some aspects, deletions comprising regions within the DNAseI hypersensitive regions of the enhancer (e.g., the +58 region of the BCL11A enhancer) are made using one or more nucleases as described herein. These deletions can comprise from about 1 nucleotide to about 551 nucleotides. Thus, the deletions can comprise, 1, 5, 10, 15, 20, 25, 30, 40, 50, 100, 150, 200, 250, 300, 350, 400, 450, 500, 550 nucleotides, or any value therebetween. In some embodiments, the deletions comprise binding regions for one or more transcription factors. In some preferred embodiments, the deletions comprise a GATA-1 binding motif, a GATA-1/TAL-1 heterodimer binding motif, or a RRBE1 binding motif.

In some embodiments, the DNA binding domains as described herein are fused to a functional domain. Some aspects include fusions of the DNA binding domains with domains capable of regulating the expression of a gene. In some embodiments, the fusion molecules (e.g., proteins or polynucleotides) comprise the DNA binding domain (e.g., Table 2, single guide RNA) fused to a gene expression modulatory domain where the modulator represses gene expression.

In some embodiments, the HSC/PC cells are contacted with the nucleases and/or DNA binding molecules of the invention (i.e., ZFPs, TALENs or CRISPR/Cas systems described herein). In some embodiments, the nucleases and/or DNA binding molecules are delivered as nucleic acids and in other embodiments, they are delivered as proteins. In some embodiments, the nucleic acids are mRNAs encoding the nucleases and/or DNA binding molecules (e.g., proteins), and in further embodiments, the mRNAs may be protected. In some embodiments, the mRNA may be chemically modified, may comprise an ARCA cap and/or may comprise a mixture of unmodified and modified nucleotides. Cells or cell lines descended from these cells are also provided, including partially or fully differentiated cells.

In some aspects, the HSC/PC are contacted with the nucleases and/or DNA binding molecules of the invention ex vivo, following apheresis of the HSC/PC from a subject, or purification from harvested bone marrow. In some embodiments, the nucleases described herein cause modifications within the BCL11A enhancer regions, for example resulting a genetically modified cell that is structurally and/or functionally distinct from wild-type and/or other modified (e.g., nuclease-modified) cells. In further embodiments, the HSC/PC containing the BCL11A enhancer region modifications are introduced back into the subject. In some instances, the HSC/PC containing the BCL11A enhancer region modifications are expanded prior to introduction. In other aspects, the genetically modified HSC/PCs are given to the subject in a bone marrow transplant wherein the HSC/PC engraft, differentiate and mature in vivo. In some embodiments, the HSC/PC are isolated from the subject following G-CSF- and/or plerixafor-induced mobilization, and in others, the cells are isolated from human bone marrow or human umbilical cords. In some aspects, the subject is treated to a mild myeloablative procedure prior to introduction of the graft comprising the modified HSC/PC, while in other aspects, the subject is treated with a vigorous myeloablative conditioning regimen. In some embodiments, the methods and compositions of the invention are used to treat or prevent a hemoglobinopathy. In some aspects, the hemoglobinopathy is a beta thalassemia, while in other aspects, the hemoglobinopathy is sickle cell disease.

In some embodiments, the HSC/PC are further contacted with a donor molecule. In some embodiments, the donor molecule is delivered by a viral vector. The donor molecule may comprise one or more sequences encoding a functional polypeptide (e.g., a cDNA or fragment thereof), with or without a promoter. Additional sequences (coding or non-coding sequences) may be included when a donor molecule is used for inactivation, including but not limited to, sequences encoding a 2A peptide, SA site, IRES, etc.

In one aspect, the methods and compositions of the invention comprise methods for contacting the HSC/PC in vivo. The nucleases and/or DNA binding proteins are delivered to HSC/PC in situ by methods known in the art. In some embodiments, the nucleases and/or DNA binding proteins of the invention comprise a viral particle that is administered to the subject in need, while in others, the nucleases and/or DNA binding proteins comprise a nanoparticle (e.g. liposome). In some embodiments, the viral particles and/or nanoparticles are delivered to the organ (e.g. bone marrow) wherein the HSC/PC reside.

In another aspect, described herein are methods of integrating a donor nucleic acid into the genome of a cell via homology-independent mechanisms. The methods comprise creating a double-stranded break (DSB) in the genome of a cell and cleaving the donor molecule using a nuclease as described herein, such that the donor nucleic acid is integrated at the site of the DSB. In certain embodiments, the donor nucleic acid is integrated via non-homology dependent methods (e.g., NHEJ). As noted above, upon in vivo cleavage the donor sequences can be integrated in a targeted manner into the genome of a cell at the location of a DSB. The donor sequence can include one or more of the same target sites for one or more of the nucleases used to create the DSB. Thus, the donor sequence may be cleaved by one or more of the same nucleases used to cleave the endogenous gene into which integration is desired. In certain embodiments, the donor sequence includes different nuclease target sites from the nucleases used to induce the DSB. DSBs in the genome of the target cell may be created by any mechanism.

In one aspect, the donor may encode a regulatory protein of interest (e.g. ZFP TFs, TALE TFs or a CRISPR/Cas TF) that binds to and/or modulates expression of a gene of interest. In one embodiment, the regulatory proteins bind to a DNA sequence and prevent binding of other regulatory factors. In another embodiment, the binding of the regulatory protein may modulate (i.e. induce or repress) expression of a target DNA. In some embodiments, the transgenic HSC/PC cell and/or animal includes a transgene that encodes a human gene. In some instances, the transgenic animal comprises a knock out at the endogenous locus corresponding to exogenous transgene, thereby allowing the development of an in vivo system where the human protein may be studied in isolation. Such transgenic models may be used for screening purposes to identify small molecules or large biomolecules or other entities which may interact with or modify the human protein of interest. In some aspects, the transgene is integrated into the selected locus (e.g., safe-harbor) into a stem cell (e.g., an embryonic stem cell, an induced pluripotent stem cell, a hematopoietic stem cell, etc.) or animal embryo obtained by any of the methods described herein, and then the embryo is implanted such that a live animal is born. The animal is then raised to sexual maturity and allowed to produce offspring wherein at least some of the offspring comprise edited endogenous gene sequence or the integrated transgene.

In another aspect, provided herein is a method of altering gene expression (e.g., BCL11A and/or a globin gene) in a cell, the method comprising: introducing, into the cell, one or more nucleases as described herein (e.g., as shown in Table 2), under conditions such that the one or more proteins are expressed and expression of the gene is altered. In certain embodiments, expression of a globin gene (e.g., gamma globin or beta globin) is altered (e.g., increased). Any of the methods described herein may further comprise integrating a donor sequence (e.g., transgene or fragment thereof under the control of an exogenous or endogenous promoter) into the genome of the cell, for example integrating a donor at or near the site of nuclease cleavage in the BCL11A gene. The donor sequence is introduced to the cell using a viral vector, as an oligonucleotide and/or on a plasmid. The cell in which gene expression is altered may be, for example, a red blood cell (RBC) precursor cell and/or a hematopoietic stem cell (e.g., CD34+ cell).

In other embodiments, provided herein is a method of producing a genetically modified cell comprising a genomic modification within an endogenous BCL11A enhancer sequence, the method comprising the steps of: a) contacting a cell with a polynucleotide (e.g. DNA or mRNA) encoding a nuclease of the invention comprising a DNA binding domain as described herein (e.g., as shown in a single row of Table 2); b) subjecting the cell to conditions conducive to expressing the nuclease from the polynucleotide; and c) modifying the endogenous BCL11A enhancer sequence with the expressed nuclease protein sufficient to produce the genetically modified cell. In certain embodiments, the cells are stimulated with at least one cytokine (e.g., prior to step (a)). The polynucleotide may be contacted with the cell using any suitable method, including but not limited, via transfection, using a non-viral vector, using a viral vector, by chemical means or by exposure to an electric field (e.g., electroporation).

Cells comprising one or a combination of the genomic modifications described herein are also provided, including cells descended from the cells produced by the methods described herein.

Also provided is a method of treating a patient in need of an increase in globin gene expression, the method comprising administering to the patient the pharmaceutical preparation (genetically modified cells, proteins and/or polynucleotides) as described herein in an amount sufficient to increase the globin gene expression in the patient. In certain embodiments, the patient is known to have, is suspected of having, or is at risk of developing a thalassemia or sickle cell disease.

A kit, comprising the nucleic acids, DNA-binding molecules, nuclease, proteins and/or genetically modified cells of the invention, is also provided. The kit may comprise nucleic acids encoding the nucleases, (e.g. RNA molecules or ZFN, TALEN or CRISPR/Cas system encoding genes contained in a suitable expression vector), or aliquots of the nuclease proteins, donor molecules, suitable stemness modifiers, cells, buffers, and/or instructions (e.g., for performing the methods of the invention) and the like. The invention includes, but is not limited to, a genetically modified cell (e.g, stem cell such as a hematopoietic (CD34+) stem cell or RBC precursor cell) comprising at least one genomic modification made by a nuclease (e.g., a nuclease as shown in a single row of Table 2), wherein the genomic modification is within an endogenous BCL11A enhancer sequence, and further wherein the genomic modification is selected from the group consisting of insertions, deletions and combinations thereof and comprises a modification at or near any of SEQ ID NOs:1 to 65 and/or SEQ ID NOs:74 to 77. In certain embodiments, the cell is a genetically modified differentiated cell descended from a stem cell as described herein (e.g., a RBC descended from a hematopoietic stem cell or RBC precursor cell).

The nuclease may comprise at least one zinc finger nuclease (ZFN) and/or at least one TALEN (e.g., as shown in Table 2) and/or a CRISPR/Cas system, and the nuclease(s) may be introduced into the cell in protein form and/or as a polynucleotide encoding the nuclease(s). In certain embodiments, the genomic modification comprises an insertion that comprises integration of a donor polynucleotide encoding a transgene. Also provided are pharmaceutical compositions comprising one or more of the genetically modified cells as described herein.

Also provided is a DNA-binding protein comprising a zinc finger protein comprising 4, 5 or 6 zinc finger domains comprising a recognition helix region, wherein the zinc finger proteins recognize a target site (or portion thereof) as shown in Tables 1 or 2 (SEQ ID NOs:1-65) and/or SEQ ID NOs:74 to 77. Also provided is a TALE proteins comprising a plurality of repeats (RVDs) as shown in Table 2 and/or a TALE protein that binds to a sequence as shown in Table 1 or 2, including a sequence comprising a portion (e.g., at least 4, 5, 6 or more) base pairs of the target sites shown in Tables 1 or 2. In some embodiments, the CRISPR/Cas system is provided as a protein-guide RNA complex. Additionally provided is a CRISPR/Cas system comprising a guide RNA that recognizes a sequence as shown in Tables 1 or 2. A fusion protein comprising a zinc finger protein or TALE protein as described herein and a wild-type or engineered cleavage domain or cleavage half-domain is also provided as are polynucleotides encoding the proteins (ZFPs, TALEs, ZFNs, TALENs) as described herein. Cells (e.g., isolated stem cells such as hematopoietic (CD34+) stem cells) comprising one or more polynucleotides and/or proteins as described herein are also provided. Also provided are kits comprising one or more proteins, polynucleotides and/or cells as described herein.

A method of altering globin gene expression in a cell (e.g., RBC precursor cell and/or hematopoietic stem cell) is also described, the method comprising: introducing, into the cell, one or more polynucleotides encoding one or more nucleases as described herein, under conditions such that the one or more proteins are expressed and expression of the globin gene (e.g., gamma and/or beta globin) is altered (e.g., increased). In certain embodiments, the methods further comprise integrating a donor sequence into the genome of the cell, for example using a viral vector, as an oligonucleotide or on a plasmid. The donor sequence may comprise a transgene under the control of an endogenous or exogenous promoter.

Also provided is a method of producing a genetically modified cell comprising a genomic modification within an endogenous BCL11A enhancer sequence (e.g., target site as shown in Table 1 or Table 2), the method comprising the steps of: (a) contacting a cell with a polynucleotide encoding a fusion protein comprising a nuclease comprising a DNA binding domain as shown in a single row of Table 2 or a nuclease that binds to any of SEQ ID NO:1-65 or 74-77; (b) subjecting the cell to conditions conducive to expressing the fusion protein from the polynucleotide; and (c) modifying the endogenous BCL11A enhancer sequence with the expressed fusion protein sufficient to produce the genetically modified cell. In certain embodiments, the method further comprises stimulating the cells with at least one cytokine. The polynucleotide(s) may be delivered inside the cell, for example using a non-viral delivery system, a viral delivery system, and/or a delivery vehicle and may comprise subjecting the cells to an electric field.

Methods of treating a patient in need of an increase in globin gene expression (e.g., a patient is known to have, is suspected of having, or is at risk of developing a globinopathy such as a thalassemia (e.g., β-thalassemia) or sickle cell disease are also provided, the method comprising administering to the patient the pharmaceutical composition as described herein (e.g., proteins, polynucleotides and/or cells) in an amount sufficient to increase the globin gene expression in the patient. In certain embodiments, the methods of altering globin gene expression in a cell (e.g., RBC precursor or hematopoietic stem cell) comprises introducing, into the cell, one or more polynucleotides as described herein, under conditions such that the one or more proteins are expressed and expression of the globin gene (gamma or beta) is altered. In certain embodiments, expression of the globin gene is increased. In certain embodiments, the polynucleotide is part of a nuclease that cleaves within the target site, the method further comprising integrating a donor sequence into the genome of the cell following cleavage by the nuclease. The donor sequence can be introduced to the cell using a viral vector, as an oligonucleotide or on a plasmid. In certain embodiments, the methods involve treating a patient in need of an increase in globin gene expression, the method comprising administering to the patient a DNA-binding molecule, nuclease and/or cell as described herein in an amount sufficient to increase the globin gene expression in the patient. In certain embodiments, the patient is known to have, is suspected of having, or is at risk of developing a globinopathy (e.g, a thalassesmia such as β-thalassemia and/or sickle cell disease.

These and other aspects will be readily apparent to the skilled artisan in light of disclosure as a whole.

BRIEF DESCRIPTION OF THE DRAWINGS

FIGS. 1A through 1C (SEQ ID NOs:68 to 70) depict the sequence of the +58 region of the BCL11A enhancer region divided into three parts for convenience. Overlaid on the figures are the footprints found for this region and putative transcription factor consensus sequence motifs.

FIG. 2 shows a schematic depicting the cleavage sites of the TALEN pairs relative to the observed footprints and the putative transcription factor binding motifs.

FIG. 4A (SEQ ID NO:71) and FIG. 4B (SEQ ID NO:72) show the target sites for the TALEN pairs 12 and 13 flanking the GATA1:TAL1 binding motif. FIG. 4C (SEQ ID NO:73) depicts the target sites for the TALEN pair 16 relative to the RREB1 binding motif.

DETAILED DESCRIPTION

Figure 1A:
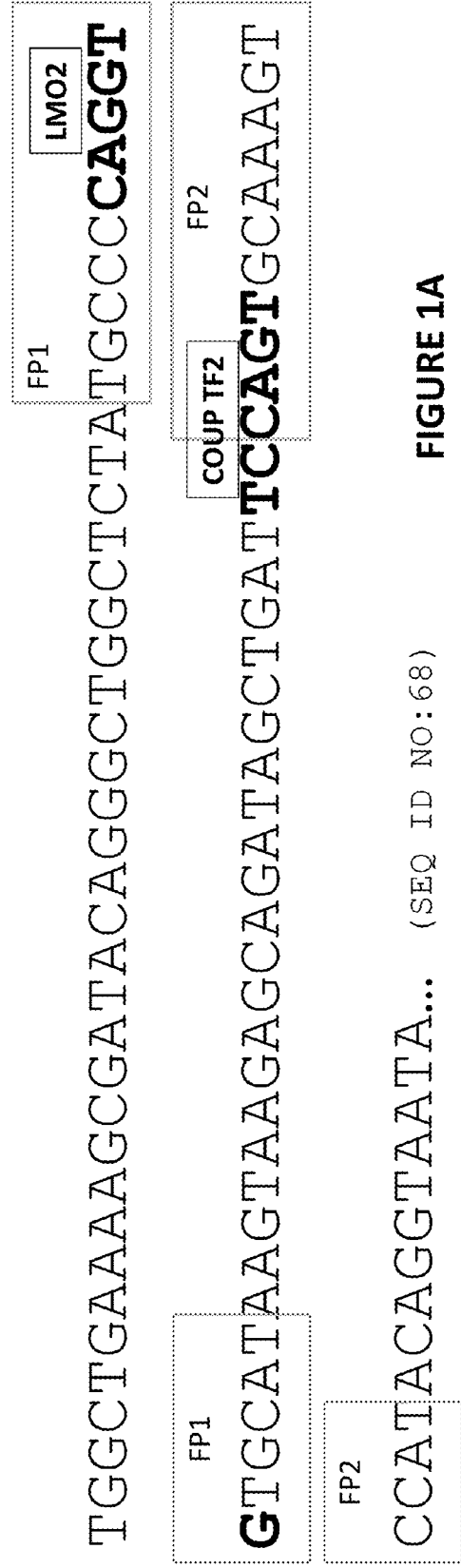

Disclosed herein are compositions and methods for genome engineering for the modulation of BCL11A and/or gamma globin expression and for the treatment and/or prevention of hemoglobinopathies. In particular, nucleases comprising the nucleases having the DNA binding domains as shown in a single row of Table 2 are efficiently achieved in HSC/PC and result in a change in relative gamma globin expression during subsequent erythropoiesis. This modulation of BCL11A and gamma globin expression is particularly useful for treatment of hemoglobinopathies (e.g., beta thalassemias, sickle cell disease) wherein there is insufficient beta globin expression or expression of a mutated form of beta-globin. Using the methods and compositions of the invention, the complications and disease related sequelae caused by the aberrant beta globin can be overcome by alteration of the expression of gamma globin in erythrocyte precursor cells.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

DEFINITIONS

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; 6,534,261 and 8,586,526; see also WO 98/53058; WO 98/53059; WO 98/53060; WO 02/016536 and WO 03/016496.

A "selected" zinc finger protein or TALE is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; 8,586,526; WO 95/19431; WO 96/06166; WO 98/53057; WO 98/54311; WO 00/27878; WO 01/60970 WO 01/88197, WO 02/099084.

"TtAgo" is a prokaryotic Argonaute protein thought to be involved in gene silencing. TtAgo is derived from the bacteria *Thermus thermophilus*. See, e.g., Swarts et al, ibid, G. Sheng et al., (2014) *Proc. Natl. Acad. Sci. U.S.A.* 111, 652). A "TtAgo system" is all the components required including, for example, guide DNAs for cleavage by a TtAgo enzyme.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break (DSB) in the target sequence (e.g., cellular chromatin) at a predetermined site. The DSB may result in deletions and/or insertions by homology-directed repair or by non-homology-directed repair mechanisms. Deletions may include any number of base pairs. Similarly, insertions may include any number of base pairs including, for example, integration of a "donor" polynucleotide, optionally having homology to the nucleotide sequence in the region of the break. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger proteins or TALEN can be used for additional double-stranded cleavage of additional target sites within the cell.

Any of the methods described herein can be used for insertion of a donor of any size and/or partial or complete inactivation of one or more target sequences in a cell by targeted integration of donor sequence that disrupts expression of the gene(s) of interest. Cell lines with partially or completely inactivated genes are also provided.

In any of the methods described herein, the exogenous nucleotide sequence (the "donor sequence" or "transgene") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474, 20070218528, 20080131962 and 20110201055, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 100,000,000 nucleotides in length (or any integer value therebetween or thereabove), preferably between about 100 and 100,000 nucleotides in length (or any integer therebetween), more preferably between about 2000 and 20,000 nucleotides in length (or any value therebetween) and even more preferable, between about 5 and 15 kb (or any value therebetween).

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster. Methods for the introduction of exogenous molecules into plant cells are known to those of skill in the art and include, but are not limited to, protoplast transformation, silicon carbide (e.g., WHISKERS™) Agrobacterium-mediated transformation, lipid-mediated transfer (i.e., liposomes, including neutral and cationic lipids), electroporation, direct injection, cell fusion, particle bombardment (e.g., using a "gene gun"), calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP, TALE or CRISPR/Cas system as described herein. Thus, gene inactivation may be partial or complete.

A "protected" mRNA is one in which the mRNA has been altered in some manner to increase the stability or translation of the mRNA. Examples of protections include the use of replacement of up to 25% of the cytodine and uridine residues with 2-thiouridine (s2U) and 5-methylcytidine (m5C). The resulting mRNA exhibits less immunogenicity and more stability as compared with its unmodified counterpart. (see Karikó et al. (2008), Molecular Therapy, Vol. 16, No. 11, pages 1833-1844). Other changes include the addition of a so-called ARCA cap, which increases the translationability of the in vitro produced mRNA (see U.S. Pat. No. 7,074,596).

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP, TALE or Cas DNA-binding domain is fused to an activation domain, the ZFP, TALE or Cas DNA-binding domain and the activation domain are in operative linkage if, in the fusion polypeptide, the ZFP, TALE of Cas DNA-binding domain portion is able to bind its target site and/or its binding site, while the activation domain is able to upregulate gene expression. When a fusion polypeptide in which a ZFP, TALE or Cas DNA-binding domain is fused to a cleavage domain, the ZFP, TALE or Cas DNA-binding domain and the cleavage domain are in operative linkage if, in the fusion polypeptide, the ZFP, TALE or Cas DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

The terms "subject" and "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the or stem cells of the invention can be administered. Subjects of the present invention include those that have been exposed to one or more chemical toxins, including, for example, a nerve toxin.

"Stemness" refers to the relative ability of any cell to act in a stem cell-like manner, i.e., the degree of toti-, pluri-, or oligo-potency and expanded or indefinite self-renewal that any particular stem cell may have.

A "target" is a DNA region in a genome or DNA sequence that has a property of interest. In some embodiments, a target is a gene or a cluster of genes. In other embodiments, a target is a sequence in a coding region of a gene, whereas in other embodiments, a target is a sequence in a non-coding region of a gene. In further embodiments, a target is in an intergenic region of a genome. A "target subsite" is a region within a target that has a characteristic of interest. In some embodiments, a target subsite is a DNA sequence recognized by a DNA binding protein (by way of non-limiting example, a ZFP, TALE or CRISPR/Cas system of the invention, or a transcription factor such as GATA-1, a GATA-1/TAL-1 heterodimer or RREB1).

Nucleases

Described herein are compositions, particularly nucleases, that are useful for in vivo cleavage of a donor molecule carrying a transgene and nucleases for cleavage of the genome of a cell such that the transgene is integrated into the genome in a targeted manner. In certain embodiments, one or more of the nucleases are naturally occurring. In other embodiments, one or more of the nucleases are non-naturally occurring, i.e., engineered in the DNA-binding domain and/or cleavage domain. For example, the DNA-binding domain of a naturally-occurring nuclease may be altered to bind to a selected target site (e.g., a meganuclease that has been engineered to bind to site different than the cognate binding site). In other embodiments, the nuclease comprises heterologous DNA-binding and cleavage domains (e.g., zinc finger nucleases; TAL-effector domain DNA binding proteins; meganuclease DNA-binding domains with heterologous cleavage domains).

A. DNA-binding Domains

Any DNA-binding domain can be used in the compositions and methods disclosed herein, including but not limited to a zinc finger DNA-binding domain, a TALE DNA binding domain, the DNA-binding portion (sgRNA) of a CRISPR/Cas nuclease, or a DNA-binding domain from a meganuclease.

In certain embodiments, the DNA binding domain of one or more of the nucleases used for in vivo cleavage and/or targeted cleavage of the genome of a cell comprises a zinc finger protein. Preferably, the zinc finger protein is non-naturally occurring in that it is engineered to bind to a target site of choice. See, for example, See, for example, Beerli et al. (2002) *Nature Biotechnol.* 20:135-141; Pabo et al. (2001) *Ann. Rev. Biochem.*70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.*10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

Nearly any linker (spacer) may be used between one or more of the components of the DNA-binding domain (e.g., zinc fingers), between one or more DNA-binding domains and/or between the DNA-binding domain and the functional domain (e.g., nuclease). Non-limiting examples of suitable linker sequences include U.S. Pat. Nos. 8,772,453; 7,888, 121; 6,479,626; 6,903,185; and 7,153,949; U.S. Publication No. 20090305419; 20150064789 and 20150132269. Thus, the proteins described herein may include any combination of suitable linkers between the individual DNA-binding components and/or between the DNA-binding domain and the functional domain of the compositions described herein.

In certain embodiments, the DNA-binding domain is part of a CRISPR/Cas nuclease system, including a single guide RNA (sgRNA) that binds to DNA. See, e.g., U.S. Pat. No. 8,697,359 and U.S. Patent Publication Nos. 20150056705 and 20150159172. The CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs functional domain (e.g., nuclease such as Cas) to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof such as derivative Cas proteins. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein. In some embodiments, the Cas protein is a small Cas9 ortholog for delivery via an AAV vector (Ran et al (2015) *Nature* 510, p. 186).

In some embodiments, the DNA binding domain is part of a TtAgo system (see Swarts et al, ibid; Sheng et al, ibid). In eukaryotes, gene silencing is mediated by the Argonaute (Ago) family of proteins. In this paradigm, Ago is bound to small (19-31 nt) RNAs. This protein-RNA silencing complex recognizes target RNAs via Watson-Crick base pairing between the small RNA and the target and endonucleolytically cleaves the target RNA (Vogel (2014) *Science* 344: 972-973). In contrast, prokaryotic Ago proteins bind to small single-stranded DNA fragments and likely function to detect and remove foreign (often viral) DNA (Yuan et al., (2005) *Mol. Cell* 19:405; Olovnikov, et al. (2013) *Mol. Cell* 51:594-605; Swarts et al., ibid). Exemplary prokaryotic Ago proteins include those from *Aquifex aeolicus, Rhodobacter sphaeroides*, and *Thermus thermophilus*.

One of the most well-characterized prokaryotic Ago protein is the one from *T. thermophilus* (TtAgo; Swarts et al. ibid). TtAgo associates with either 15 nt or 13-25 nt single-stranded DNA fragments with 5' phosphate groups. This "guide DNA" bound by TtAgo serves to direct the protein-DNA complex to bind a Watson-Crick complementary DNA sequence in a third-party molecule of DNA. Once the sequence information in these guide DNAs has allowed identification of the target DNA, the TtAgo-guide DNA complex cleaves the target DNA. Such a mechanism is also supported by the structure of the TtAgo-guide DNA complex while bound to its target DNA (G. Sheng et al., ibid). Ago from *Rhodobacter sphaeroides* (RsAgo) has similar properties (Olivnikov et al. ibid).

Exogenous guide DNAs of arbitrary DNA sequence can be loaded onto the TtAgo protein (Swarts et al. ibid.). Since the specificity of TtAgo cleavage is directed by the guide DNA, a TtAgo-DNA complex formed with an exogenous, investigator-specified guide DNA will therefore direct TtAgo target DNA cleavage to a complementary investigator-specified target DNA. In this way, one may create a targeted double-strand break in DNA. Use of the TtAgo-guide DNA system (or orthologous Ago-guide DNA systems from other organisms) allows for targeted cleavage of genomic DNA within cells. Such cleavage can be either single- or double-stranded. For cleavage of mammalian genomic DNA, it would be preferable to use of a version of TtAgo codon optimized for expression in mammalian cells. Further, it might be preferable to treat cells with a TtAgo-DNA complex formed in vitro where the TtAgo protein is fused to a cell-penetrating peptide. Further, it might be preferable to use a version of the TtAgo protein that has been altered via mutagenesis to have improved activity at 37° C. Ago-RNA-mediated DNA cleavage could be used to affect a panopoly of outcomes including gene knock-out, targeted gene addition, gene correction, targeted gene deletion using techniques standard in the art for exploitation of DNA breaks.

Thus, any DNA-binding domain can be used.

B. Cleavage Domains

Any suitable cleavage domain can be operatively linked to the DNA-binding domains as described herein to form a nuclease. The cleavage domain may be heterologous to the DNA-binding domain, for example a zinc finger DNA-binding domain and a cleavage domain from a nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.*25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is FokI. This particular enzyme is active as a dimer. Bitinaite et al. (1998) *Proc. Natl. Acad. Sci. USA* 95:10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in U.S. Pat. No. 7,888,121 incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in See, e.g., U.S. Pat. Nos. 7,914,796; 8,034,598 and 8,623,618, the disclosures of all of which are incorporated by reference in their entireties herein. Amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains.

Exemplary engineered cleavage half-domains of FokI that form obligate heterodimers include a pair in which a first cleavage half-domain includes mutations at amino acid residues at positions 490 and 538 of FokI and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E: I499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively. See, e.g., U.S. Pat. Nos. 7,914,796; 8,034,598 and 8,623,618. In other embodiments, the engineered cleavage half domain comprises the "Sharkey" and/or "Sharkey'" mutations (see Guo et al, (2010) *J Mol. Biol.* 400(1):96-107).

Engineered cleavage half-domains described herein can be prepared using any suitable method, for example, by site-directed mutagenesis of wild-type cleavage half-domains (Fok I) as described in U.S. Pat. Nos. 7,888,121; 7,914,796; 8,034,598 and 8,623,618.

Alternatively, nucleases may be assembled in vivo at the nucleic acid target site using so-called "split-enzyme" technology (see, e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in WO 2009/042163 and 20090068164. Expression of the nuclease may be under the control of a constitutive promoter or an inducible promoter, for example the galactokinase promoter which is activated (de-repressed) in the presence of raffinose and/or galactose and repressed in presence of glucose.

In some embodiments, the nuclease is a self-inactivating (see Epstein and Schaffer, (2016) ASGCT poster abstract 119).

The nuclease(s) may make one or more double-stranded and/or single-stranded cuts in the target site. In certain embodiments, the nuclease comprises a catalytically inactive cleavage domain (e.g., FokI and/or Cas protein). See, e.g., U.S. Pat. Nos. 9,200,266; 8,703,489 and Guillinger et al. (2014) *Nature Biotech.* 32(6):577-582. The catalytically inactive cleavage domain may, in combination with a catalytically active domain act as a nickase to make a single-stranded cut. Therefore, two nickases can be used in combination to make a double-stranded cut in a specific region. Additional nickases are also known in the art, for example, McCaffrey et al. (2016) *Nucleic Acids Res.* 44(2):e11. doi: 10.1093/nar/gkv878. Epub 2015 Oct. 19.

The CRISPR/Cas System

In certain embodiments, the nuclease or DNA-binding molecule comprises a CRISPR/Cas nuclease or DNA-binding system.

The Type II CRISPR, initially described in *S. pyogenes*, is one of the most well characterized CRISPR/Cas systems (see Jinek et al (2012) *Science* 337:816 and Cong et al (2013) Sciencexpress/10.1126/science.1231143) and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences where processing occurs by a double strand-specific RNase III in the presence of the Cas9 protein. Third, the mature crRNA: tracrRNA complex directs Cas9 to the target DNA via Watson-Crick base-pairing between the spacer on the crRNA and the protospacer on the target DNA next to the protospacer adjacent motif (PAM), an additional requirement for target recognition. In addition, the tracrRNA must also be present as it base pairs with the crRNA at its 3' end, and this association triggers Cas9 activity. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation,' (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system.

Type II CRISPR systems have been found in many different bacteria. BLAST searches on publically available genomes by Fonfara et al (2013) *Nuc Acid Res* 42(4):2377-2590) found Cas9 orthologs in 347 species of bacteria. Additionally, this group demonstrated in vitro CRISPR/Cas cleavage of a DNA target using Cas9 orthologs from *S. pyogenes, S. mutans, S. therophilus, C. jejuni, N. meningitides, P. multocida* and *F. novicida*. Thus, the term "Cas9" refers to an RNA guided DNA nuclease comprising a DNA binding domain and two nuclease domains, where the gene encoding the Cas9 may be derived from any suitable bacteria.

The Cas9 protein includes a recognition lobe that is involved in binding sgRNA and DNA and a nuclease lobe that includes a domain involved in interaction with the PAM sequence. See, e.g., Nishimasu et al. (2014) *Cell* 156(5): 9325-949). The Cas9 protein has at least two nuclease domains: one nuclease domain is similar to a HNH endonuclease, while the other resembles a Ruv endonuclease domain. The HNH-type domain appears to be responsible for cleaving the DNA strand that is complementary to the crRNA while the Ruv domain cleaves the non-complementary strand. The Cas 9 nuclease can be engineered such that only one of the nuclease domains is functional, creating a Cas nickase (see Jinek et al, ibid). Nickases can be generated by specific mutation of amino acids in the catalytic domain of the enzyme, or by truncation of part or all of the domain such that it is no longer functional. Since Cas 9 comprises two nuclease domains, this approach may be taken on either domain. A double strand break can be achieved in the target DNA by the use of two such Cas 9 nickases. The nickases will each cleave one strand of the DNA and the use of two will create a double strand break.

The requirement of the crRNA-tracrRNA complex can be avoided by use of an engineered "single-guide RNA" (sgRNA) that comprises the hairpin normally formed by the annealing of the crRNA and the tracrRNA (see Jinek ibid), and see below for more discussion. In *S. pyogenes*, the engineered tracrRNA:crRNA fusion, or the sgRNA, guides Cas9 to cleave the target DNA when a double strand RNA:DNA heterodimer forms between the Cas associated RNAs and the target DNA. This system comprising the Cas9 protein and an engineered sgRNA containing a PAM sequence has been used for RNA guided genome editing and has been useful for zebrafish embryo genomic editing in vivo (see Hwang et al (2013) *Nature Biotechnology* 31 (3):227) with editing efficiencies similar to ZFNs and TAL-ENs.

The Cas9 protein from *S. pyogenes* has been crystallized in association with its guide RNA and target DNA (Nishimasu et al (2014) *Cell* 156(5): 935-949). This study confirmed that the PAM-interacting (PI) residues in Cas9 are found within the so-called recognition lobe (REC) of the protein. The PI location appears to be residues 1099-1368 of the protein and is suggested to recognize the PAM sequence on the non-complementary DNA strand in the target region. The work also included the swapping of PI domains from *S. pyogenes* and *S. thermophilus*, resulting in chimeric Cas9 proteins that were able to recognize PAM sequences specific to the identity of the PI sequence rather than the rest of the Cas9 protein. In addition, deletion of the PI domain all together resulted in Cas9 proteins devoid of activity, demonstrating that PI domain is essential for Cas9 function.

Further, the CRISPR/Cas system can be used to inhibit gene expression. Lei et al (see, (2013) *Cell*, 152, (5):1173-1183) have shown that a catalytically dead Cas9 lacking endonuclease activity, when co-expressed with a guide RNA, generates a DNA recognition complex that can specifically interfere with transcriptional elongation, RNA polymerase binding, or transcription factor binding. This system, called CRISPR interference (CRISPRi), can efficiently repress expression of targeted genes.

RNA Components of CRISPR/Cas

Chimeric or sgRNAs can be engineered to comprise a sequence complementary to any desired target. The RNAs comprise 22 bases of complementarity to a target and of the form G[n19], followed by a protospacer-adjacent motif (PAM) of the form NGG. Thus, in one method, sgRNAs can be designed by utilization of a known ZFN target in a gene of interest by (i) aligning the recognition sequence of the ZFN heterodimer with the reference sequence of the relevant genome (human, mouse, or of a particular plant species); (ii) identifying the spacer region between the ZFN half-sites; (iii) identifying the location of the motif G[N20]GG that is closest to the spacer region (when more than one such motif overlaps the spacer, the motif that is centered relative to the spacer is chosen); (iv) using that motif as the core of the sgRNA. This method advantageously relies on proven nuclease targets. Alternatively, sgRNAs can be designed to target any region of interest simply by identifying a suitable target sequence the conforms to the G[n20]GG formula. Along with the complementarity region, an sgRNA may comprise additional nucleotides to extend to tail region of the tracrRNA portion of the sgRNA (see Hsu et al (2013) *Nature Biotech* doi:10.1038/nbt.2647). Tails may be of +67 to +85 nucleotides, or any number therebetween with a preferred length of +85 nucleotides. Truncated sgRNAs may also be used, "tru-gRNAs" (see Fu et al, (2014) *Nature Biotech* 32(3): 279). In tru-gRNAs, the complementarity region is diminished to 17 or 18 nucleotides in length.

Further, alternative PAM sequences may also be utilized, where a PAM sequence can be NAG as an alternative to NGG (Hsu 2014, ibid) using a *S. pyogenes* Cas9. Additional PAM sequences may also include those lacking the initial G (Sander and Joung (2014) *Nature Biotech* 32(4):347). In addition to the *S. pyogenes* encoded Cas9 PAM sequences, other PAM sequences can be used that are specific for Cas9 proteins from other bacterial sources. For example, the PAM sequences shown below (adapted from Sander and Joung, ibid, and Esvelt et al, (2013) *Nat Meth* 10(11):1116) are specific for these Cas9 proteins:

| Species | PAM |
| --- | --- |
| S. pyogenes | NGG |
| S. pyogenes | NAG |
| S. mutans | NGG |
| S. thermophilius | NGGNG |
| S. thermophilius | NNAAAW |
| S. thermophilius | NNAGAA |
| S. thermophilius | NNNGATT |
| C. jejuni | NNNNACA |
| N. meningitides | NNNNGATT |
| P. multocida | GNNNCNNA |
| F. novicida | NG |

Thus, a suitable target sequence for use with a *S. pyogenes* CRISPR/Cas system can be chosen according to the following guideline: [n17, n18, n19, or n20](G/A)G. Alternatively the PAM sequence can follow the guideline G[n17, n18, n19, n20](G/A)G. For Cas9 proteins derived from non-*S. pyogenes* bacteria, the same guidelines may be used where the alternate PAMs are substituted in for the *S. pyogenes* PAM sequences. Additionally, a Cas9 protein may be modified such that it recognizes a PAM sequence from another bacterial species, or such that it recognizes an entirely novel PAM (see U.S. Publication No. 20150353917).

Most preferred is to choose a target sequence with the highest likelihood of specificity that avoids potential off target sequences. These undesired off target sequences can be identified by considering the following attributes: i) similarity in the target sequence that is followed by a PAM sequence known to function with the Cas9 protein being utilized; ii) a similar target sequence with fewer than three mismatches from the desired target sequence; iii) a similar target sequence as in ii), where the mismatches are all located in the PAM distal region rather than the PAM proximal region (there is some evidence that nucleotides 1-5 immediately adjacent or proximal to the PAM, sometimes referred to as the 'seed' region (Wu et al (2014) *Nature Biotech* doi:10.1038/nbt2889) are the most critical for recognition, so putative off target sites with mismatches located in the seed region may be the least likely be recognized by the sg RNA); and iv) a similar target sequence where the mismatches are not consecutively spaced or are spaced greater than four nucleotides apart (Hsu 2014, ibid). Thus, by performing an analysis of the number of potential off target sites in a genome for whichever CRIPSR/Cas system is being employed, using these criteria above, a suitable target sequence for the sgRNA may be identified.

In some embodiments, the CRISPR-Cfp1 system is used. The CRISPR-Cfp1 system, identified in *Francisella* spp, (Fn) is a class 2 CRISPR-Cas system that mediates robust DNA interference in human cells. Although functionally conserved, Cfp1 and Cas9 differ in many aspects including in their guide RNAs and substrate specificity (see Fagerlund et al, (2015) *Genom Bio* 16:251). A major difference between Cas9 and Cfp1 proteins is that Cfp1 does not utilize tracrRNA, and thus requires only a crRNA. The FnCfp1 crRNAs are 42-44 nucleotides long (19-nucleotide repeat and 23-25-nucleotide spacer) and contain a single stem-loop, which tolerates sequence changes that retain secondary structure. In addition, the Cfp1 crRNAs are significantly shorter than the ~100-nucleotide engineered sgRNAs required by Cas9, and the PAM requirements for FnCfp1 are 5'-TTN-3' and 5'-CTA-3' on the displaced strand. Although both Cas9 and Cfp1 make double strand breaks in the target DNA, Cas9 uses its RuvC- and HNH-like domains to make blunt-ended cuts within the seed sequence of the guide RNA, whereas Cfp1 uses a RuvC-like domain to produce staggered cuts outside of the seed. Because Cfp1 makes staggered cuts away from the critical seed region, NHEJ will not disrupt the target site, therefore ensuring that Cfp1 can continue to cut the same site until the desired HDR recombination event has taken place. Thus, in the methods and compositions described herein, it is understood that the term "'Cas" includes both Cas9 and Cfp1 proteins. Thus, as used herein, a "CRISPR/Cas system" refers both CRISPR/Cas and/or CRISPR/Cfp1 systems, including both nuclease and/or transcription factor systems.

Target Sites

As described in detail above, DNA domains can be engineered to bind to any sequence of choice. An engineered DNA-binding domain can have a novel binding specificity, compared to a naturally-occurring DNA-binding domain. In certain embodiments, the DNA-binding domains bind to a sequence within a BCL11A enhancer sequence, for example a target site (typically 9, 10, 11, 12, 13, 14, 15, 16, 17, 18, 19, 20, 21 or even more base pairs) is between exon 2 and exon 3 of BCL11A, including DNA-binding domains that bind to a sequence within a DNAseI hypersensitive site in the BCL11A enhancer sequence (e.g., +58) as shown in Table 1 or Table 2. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties. Rational design of TAL-effector domains can also be performed. See, e.g., U.S. Publication No. 20110301073.

Exemplary selection methods applicable to DNA-binding domains, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

Selection of target sites; nucleases and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, DNA-binding domains (e.g., multi-fingered zinc finger proteins) and/or fusions of DNA-binding domain(s) and functional domain(s) may be linked together using any suitable linker sequences, including for example, linkers of 5 or more amino acids. U.S. Pat. Nos. 8,772,453; 7,888,121 (e.g., "ZC" linker); U.S. Pat. Nos. 6,479,626; 6,903,185; and 7,153,949; U.S. Publication Nos. 20090305419and 20150064789. The proteins described herein may include any combination of suitable linkers between the individual DNA-binding domains of the protein. See, also, U.S. Pat. No. 8,586,526.

Donors

In certain embodiments, the present disclosure relates to nuclease-mediated targeted integration of an exogenous sequence into the genome of a cell using the BCL11A enhancer region-binding molecules described herein. As noted above, insertion of an exogenous sequence (also called a "donor sequence" or "donor" or "transgene"), for example for deletion of a specified region and/or correction of a mutant gene or for increased expression of a wild-type gene. It will be readily apparent that the donor sequence is typically not identical to the genomic sequence where it is placed. A donor sequence can contain a non-homologous sequence flanked by two regions of homology to allow for efficient HDR at the location of interest or can be integrated via non-homology directed repair mechanisms. Additionally, donor sequences can comprise a vector molecule containing sequences that are not homologous to the region of interest in cellular chromatin. A donor molecule can contain several, discontinuous regions of homology to cellular chromatin, and, for example, lead to a deletion of a BCL11A enhancer region (or a fragment therereof) when used as a substrate for repair of a DBS induced by one of the nucleases described here. Further, for targeted insertion of sequences not normally present in a region of interest, said sequences can be present in a donor nucleic acid molecule and flanked by regions of homology to sequence in the region of interest.

Polynucleotides for insertion can also be referred to as "exogenous" polynucleotides, "donor" polynucleotides or molecules or "transgenes." The donor polynucleotide can be DNA or RNA, single-stranded and/or double-stranded and can be introduced into a cell in linear or circular form. See, e.g., U.S. Patent Publication Nos. 20100047805 and 20110207221. The donor sequence(s) are preferably contained within a DNA MC, which may be introduced into the cell in circular or linear form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. If introduced in double-stranded form, the donor may include one or more nuclease target sites, for example, nuclease target sites flanking the transgene to be integrated into the cell's genome. See, e.g., U.S. Patent Publication No. 20130326645.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

In certain embodiments, the double-stranded donor includes sequences (e.g., coding sequences, also referred to as transgenes) greater than 1 kb in length, for example between 2 and 200 kb, between 2 and 10 kb (or any value therebetween). The double-stranded donor also includes at least one nuclease target site, for example. In certain embodiments, the donor includes at least 2 target sites, for example for a pair of ZFNs or TALENs. Typically, the nuclease target sites are outside the transgene sequences, for example, 5' and/or 3' to the transgene sequences, for cleavage of the transgene. The nuclease cleavage site(s) may be for any nuclease(s). In certain embodiments, the nuclease target site(s) contained in the double-stranded donor are for the same nuclease(s) used to cleave the endogenous target into which the cleaved donor is integrated via homology-independent methods.

The donor is generally inserted so that its expression is driven by the endogenous promoter at the integration site, namely the promoter that drives expression of the endogenous gene into which the donor is inserted (e.g., globin, AAVS1, etc.). However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. In other embodiments, the transgene (e.g., with or without globin encoding sequences) is integrated into any endogenous locus, for example a safe-harbor locus. See, e.g., U.S. Patent Publications 20080299580; 20080159996 and 20100218264.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

The transgenes carried on the donor sequences described herein may be isolated from plasmids, cells or other sources using standard techniques known in the art such as PCR. Donors for use can include varying types of topology, including circular supercoiled, circular relaxed, linear and the like. Alternatively, they may be chemically synthesized using standard oligonucleotide synthesis techniques. In addition, donors may be methylated or lack methylation. Donors may be in the form of bacterial or yeast artificial chromosomes (BACs or YACs).

The double-stranded donor polynucleotides described herein may include one or more non-natural bases and/or backbones. In particular, insertion of a donor molecule with methylated cytosines may be carried out using the methods described herein to achieve a state of transcriptional quiescence in a region of interest.

The exogenous (donor) polynucleotide may comprise any sequence of interest (exogenous sequence). Exemplary exogenous sequences include, but are not limited to any polypeptide coding sequence (e.g., cDNAs), promoter sequences, enhancer sequences, epitope tags, marker genes, cleavage enzyme recognition sites and various types of expression constructs. Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence.

In a preferred embodiment, the exogenous sequence (transgene) comprises a polynucleotide encoding any polypeptide of which expression in the cell is desired, including, but not limited to antibodies, antigens, enzymes, receptors (cell surface or nuclear), hormones, lymphokines, cytokines, reporter polypeptides, growth factors, and functional fragments of any of the above. The coding sequences may be, for example, cDNAs.

For example, the exogenous sequence may comprise a sequence encoding a polypeptide that is lacking or non-functional in the subject having a genetic disease, including but not limited to any of the following genetic diseases: achondroplasia, achromatopsia, acid maltase deficiency, adenosine deaminase deficiency (OMIM No. 102700), adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasiaossificans progressive, fragile X syndrome, galactosemis, Gaucher's disease, generalized gangliosidoses (e.g., GM1), hemochromatosis, the hemoglobin C mutation in the $6^{th}$ codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency (LAD, OMIM No. 116920), leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, *porphyria*, Prader-Willi syndrome, progeria, Proteus syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240).

Additional exemplary diseases that can be treated by targeted integration include acquired immunodeficiencies, lysosomal storage diseases (e.g., Gaucher's disease, GM1, Fabry disease and Tay-Sachs disease), mucopolysaccahidosis (e.g. Hunter's disease, Hurler's disease), hemoglobinopathies (e.g., sickle cell diseases, HbC, α-thalassemia, β-thalassemia) and hemophilias.

In certain embodiments, the exogenous sequences can comprise a marker gene (described above), allowing selection of cells that have undergone targeted integration, and a linked sequence encoding an additional functionality. Non-limiting examples of marker genes include GFP, drug selection marker(s) and the like.

Additional gene sequences that can be inserted may include, for example, wild-type genes to replace mutated sequences. For example, a wild-type Factor IX gene sequence may be inserted into the genome of a stem cell in which the endogenous copy of the gene is mutated. The wild-type copy may be inserted at the endogenous locus, or may alternatively be targeted to a safe harbor locus.

Construction of such expression cassettes, following the teachings of the present specification, utilizes methodologies well known in the art of molecular biology (see, for example, Ausubel or Maniatis). Before use of the expression cassette to generate a transgenic animal, the responsiveness of the expression cassette to the stress-inducer associated with selected control elements can be tested by introducing the expression cassette into a suitable cell line (e.g., primary cells, transformed cells, or immortalized cell lines).

Furthermore, although not required for expression, exogenous sequences may also transcriptional or translational regulatory sequences, for example, promoters, enhancers, insulators, internal ribosome entry sites, sequences encoding 2A peptides and/or polyadenylation signals. Further, the control elements of the genes of interest can be operably linked to reporter genes to create chimeric genes (e.g., reporter expression cassettes).

Targeted insertion of non-coding nucleic acid sequence may also be achieved. Sequences encoding antisense RNAs, RNAi, shRNAs and micro RNAs (miRNAs) may also be used for targeted insertions.

In additional embodiments, the donor nucleic acid may comprise non-coding sequences that are specific target sites for additional nuclease designs. Subsequently, additional nucleases may be expressed in cells such that the original donor molecule is cleaved and modified by insertion of another donor molecule of interest. In this way, reiterative integrations of donor molecules may be generated allowing for trait stacking at a particular locus of interest or at a safe harbor locus.

Delivery

The nucleases as described herein (e.g., Table 2 or sgRNA), polynucleotides encoding these nucleases, donor polynucleotides and compositions comprising the proteins and/or polynucleotides described herein may be delivered in vivo or ex vivo by any suitable means into any cell type.

Suitable cells include eukaryotic (e.g., animal) and prokaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as *Spodoptera fugiperda* (Sf), or fungal cells such as *Saccharomyces, Pichia* and *Schizosaccharomyces*. In certain embodiments, the cell line is a CHO, MDCK or HEK293 cell line. Suitable cells also include stem cells such as, by way of example, embryonic stem cells, induced pluripotent stem cells, hematopoietic stem cells, neuronal stem cells and mesenchymal stem cells.

Methods of delivering nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using vectors containing sequences encoding one or more of the ZFN(s), described herein. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more of the sequences needed for treatment. Thus, when one or more nucleases and a donor construct are introduced into the cell, the nucleases and/or donor polynucleotide may be carried on the same vector or on different vectors (DNA MC(s)). When multiple vectors are used, each vector may comprise a sequence encoding one or multiple nucleases and/or donor constructs. Conventional viral and non-viral based gene transfer methods can be used to introduce nucleic acids encoding nucleases and/or donor constructs in cells (e.g., mammalian cells) and target tissues. Non-viral vector delivery systems include DNA or RNA plasmids, DNA MCs, naked nucleic acid, and nucleic acid complexed with a delivery vehicle such as a liposome or poloxamer. Suitable non-viral vectors include nanotaxis vectors, including vectors commercially available from InCellArt (France). Viral vector delivery systems include DNA and RNA viruses, which have either episomal or integrated genomes after delivery to the cell. For a review of in vivo delivery of engineered DNA-binding proteins and fusion proteins comprising these binding proteins, see, e.g., Rebar (2004) *Expert Opinion Invest. Drugs* 13(7):829-839; Rossi et al. (2007) *Nature Biotech.* 25(12):1444-1454 as well as general gene delivery references such as Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc., (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787). In some embodiments, nucleic acids encoding nucleases, transcription factors, guide RNAs, donor etc. are delivered using a lipid nanoparticle (see e.g. WO2015199952).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) *Nature Biotechnology* 27(7):643).

The use of RNA or DNA viral based systems for the delivery of nucleic acids encoding engineered ZFPs, TALEs and/or CRISPR/Cas systems take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV2, AAV3, AAV4, AAV5, AAV6, AAV7, AAV8, AAV9 and AAVrh.10 and any novel AAV serotype can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides (e.g. nuclease-encoding and/or double-stranded donors) described herein include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222; U.S. Patent Publication No 2009/0117617.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences*, 17th ed., 1989).

It will be apparent that the nuclease-encoding sequences and donor constructs can be delivered using the same or different systems. For example, the nucleases and donors can be carried by the same DNA MC. Alternatively, a donor polynucleotide can be carried by a MC, while the one or more nucleases can be carried by a standard plasmid or AAV vector. Furthermore, the different vectors can be administered by the same or different routes (intramuscular injection, tail vein injection, other intravenous injection, intraperitoneal administration and/or intramuscular injection. The vectors can be delivered simultaneously or in any sequential order. IN some embodiments, the nuclease or transcription factor is delivered to the cell as a polypeptide or a polypeptide/guide RNA complex (see Liu et al (2015) *Nat. Protocol.* 10:1842-1859).

Thus, the instant disclosure includes in vivo or ex vivo treatment of diseases and conditions that are amenable to insertion of a transgenes encoding a therapeutic protein. The compositions are administered to a human patient in an amount effective to obtain the desired concentration of the therapeutic polypeptide in the serum or the target organ or cells. Administration can be by any means in which the polynucleotides are delivered to the desired target cells. For example, both in vivo and ex vivo methods are contemplated. Intravenous injection to the portal vein is a preferred method of administration. Other in vivo administration modes include, for example, direct injection into the lobes of the liver or the biliary duct and intravenous injection distal to the liver, including through the hepatic artery, direct injection in to the liver parenchyma, injection via the hepatic artery, and/or retrograde injection through the biliary tree. Ex vivo modes of administration include transduction in vitro of resected hepatocytes or other cells of the liver, followed by infusion of the transduced, resected hepatocytes back into the portal vasculature, liver parenchyma or biliary tree of the human patient, see e.g., Grossman et al., (1994) *Nature Genetics*, 6:335-341.

The effective amount of nuclease(s) and donor to be administered will vary from patient to patient and according to the therapeutic polypeptide of interest. Accordingly, effective amounts are best determined by the physician administering the compositions and appropriate dosages can be determined readily by one of ordinary skill in the art. After allowing sufficient time for integration and expression (typically 4-15 days, for example), analysis of the serum or other tissue levels of the therapeutic polypeptide and comparison to the initial level prior to administration will determine whether the amount being administered is too low, within the right range or too high. Suitable regimes for initial and subsequent administrations are also variable, but are typified by an initial administration followed by subsequent administrations if necessary. Subsequent administrations may be administered at variable intervals, ranging from daily to annually to every several years. One of skill in the art will appreciate that appropriate immunosuppressive techniques may be recommended to avoid inhibition or blockage of transduction by immunosuppression of the delivery vectors, see e.g., Vilquin et al., (1995) *Human Gene Ther.*, 6:1391-1401.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

Cells

Also described herein are cells and/or cell lines in which an endogenous BCL11A enhancer sequence is modified by the nucleases described herein (e.g., Table 2). The modification may be, for example, as compared to the wild-type sequence of the cell. The cell or cell lines may be heterozygous or homozygous for the modification. The modifications to the BCL11A sequence may comprise insertions, deletions and/or combinations thereof.

The modification is preferably within, at or near the nuclease(s) binding and/or cleavage site(s), for example, to one or more nucleotides within the binding and/or target site(s) and/or 1-300 (or any value therebetween) base pairs upstream or downstream of the site(s) of binding/cleavage, more preferably within 1-100 base pairs (or any value therebetween) of either side of the binding and/or cleavage site(s), even more preferably within 1 to 50 base pairs (or any value therebetween) on either side of the binding and/or cleavage site(s). In certain embodiments, the modification is at or near the "+58" region of the BCL11A enhancer, for example, at or near a nuclease binding site shown in any of SEQ ID NO:1-65 and/or SEQ ID NOs:74 to 77.

Any cell or cell line may be modified, for example a stem cell, for example an embryonic stem cell, an induced pluripotent stem cell, a hematopoietic stem cell, a neuronal stem cell and a mesenchymal stem cell. Other non-limiting examples of cells as described herein include T-cells (e.g., CD4+, CD3+, CD8+, etc.); dendritic cells; B-cells. A descendent of a stem cell, including a partially or fully differentiated cell, is also provided (e.g., a RBC or RBC precursor cell). Non-limiting examples other cell lines including a modified BCL11A sequence include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as *Spodopterafugiperda* (Sf), or fungal cells such as *Saccharomyces, Pichia* and *Schizosaccharomyces*.

The cells as described herein are useful in treating and/or preventing a disorder, for example, by ex vivo therapies. The nuclease-modified cells can be expanded and then reintroduced into the patient using standard techniques. See, e.g., Tebas et al (2014) *New Eng J Med* 370(10):901. In the case of stem cells, after infusion into the subject, in vivo differentiation of these precursors into cells expressing the functional transgene also occurs. Pharmaceutical compositions comprising the cells as described herein are also provided. In addition, the cells may be cryopreserved prior to administration to a patient.

Any of the modified cells or cell lines disclosed herein may show increased expression of gamma globin. Compositions such as pharmaceutical compositions comprising the genetically modified cells as described herein are also provided Applications The methods and compositions disclosed herein are for modifying expression of protein, or correcting an aberrant gene sequence that encodes a protein expressed in a genetic disease, such as a sickle cell disease or a thalassemia. Thus, the methods and compositions provide for the treatment and/or prevention of such genetic diseases. Genome editing, for example of stem cells, can be used to correct an aberrant gene, insert a wild type gene, or change the expression of an endogenous gene. By way of non-limiting example, a wild type gene, e.g. encoding at least one globin (e.g., α and/or β globin), may be inserted into a cell (e.g., into an endogenous BCL11A enhancer sequence using one or more nucleases as described herein) to provide the globin proteins deficient and/or lacking in the cell and thereby treat a genetic disease, e.g., a hemoglobinopathy, caused by faulty globin expression. Alternatively or in addition, genomic editing with or without administration of the appropriate donor, can correct the faulty endogenous gene, e.g., correcting the point mutation in α- or β-hemoglobin, to restore expression of the gene and/or treat a genetic disease, e.g. sickle cell disease and/or knock out or alteration (overexpression or repression) of any direct or indirect globin regulatory gene (e.g. inactivation of the γ globin-regulating gene BCL11A or the BCL11A-regulator KLF1). Specifically, the methods and compositions of the invention have use in the treatment or prevention of hemoglobinopathies.

The nucleases of the invention are targeted to the BCL11A enhancer region, known to be required for the expression of BCL11A, and hence the down regulation of gamma globin expression. Modification of this enhancer region may result in erythrocytes with increased gamma globin expression, and thus may be helpful for the treatment or prevention of sickle cell disease or beta thalassemia.

The following Examples relate to exemplary embodiments of the present disclosure in which the nuclease comprises a TALE nuclease (TALEN). It will be appreciated that this is for purposes of exemplification only and that other nucleases can be used, for example ZFN, TtAgo and CRISPR/Cas systems, homing endonucleases (meganucleases) with engineered DNA-binding domains and/or fusions of naturally occurring of engineered homing endonucleases (meganucleases) DNA-binding domains and heterologous cleavage domains and/or fusions of meganucleases and TALE proteins.

EXAMPLES

Example 1

Assembly of TALE Nucleases

TALENs were assembled as described in Miller et al (2011) *Nature Biotechnology* 29 (2): 143-151. Additionally, see co-owned U.S. Patent Publication No. 20140093913 and U.S. Pat. No. 8,586,526. The TALENs were assembled with the +63 architecture.

Example 2

Footprint Analysis of the +58 Region of the BCL11A Enhancer

To probe the +58 region for the binding of potential transcription factors, footprint analysis in human erythroblasts was performed as described in Neph et al (2012), *Nature* 489:83-90. The analysis provided evidence of 8 footprint regions in the +58 DNAse I hypersensitive region of the BCL11A erythroid enhancer indicating the potential binding of regulatory proteins across the region. The footprints and genome coordinates (relative to UCSC Genome Assembly hg19) are shown below in Table 1:

TABLE 1

Footprints identified on the +58 enhancer region

| Footprint number | Sequence (5'-3') | SEQ ID NO | Coordinates |
|---|---|---|---|
| 1 | TGCCCCAGGTGTGCAT | 4 | chr2:60,722,552-60,722,568 |
| 2 | CAGTGCAAAGTCCAT | 5 | chr2:60,722,514-60,722,528 |
| 3 | GGCCAGAAAAGAGATATGGCATCTAC | 6 | chr2:60,722,473-60,722,498 |
| 4 | ACACACCAGGGTCAATACAAC | 7 | chr2:60,722,441-60,722,461 |
| 5 | ACAGTTGCTTTTATC | 8 | chr2:60,722,401-60,722,415 |
| 6 | CTCCAGGAAGGGTTTGGC | 9 | chr2:60,722,378-60,722,395 |
| 7 | AGGGTGGGGCGTGGGTGGGGT | 10 | chr2:60,722,348-60,722,369 |
| 8 | TCTCCATCGGTGGCCGTTTGCCCAGGGGGCCTCTTT | 11 | chr2:60,722,292-60,722,328 |

Figure 1B:
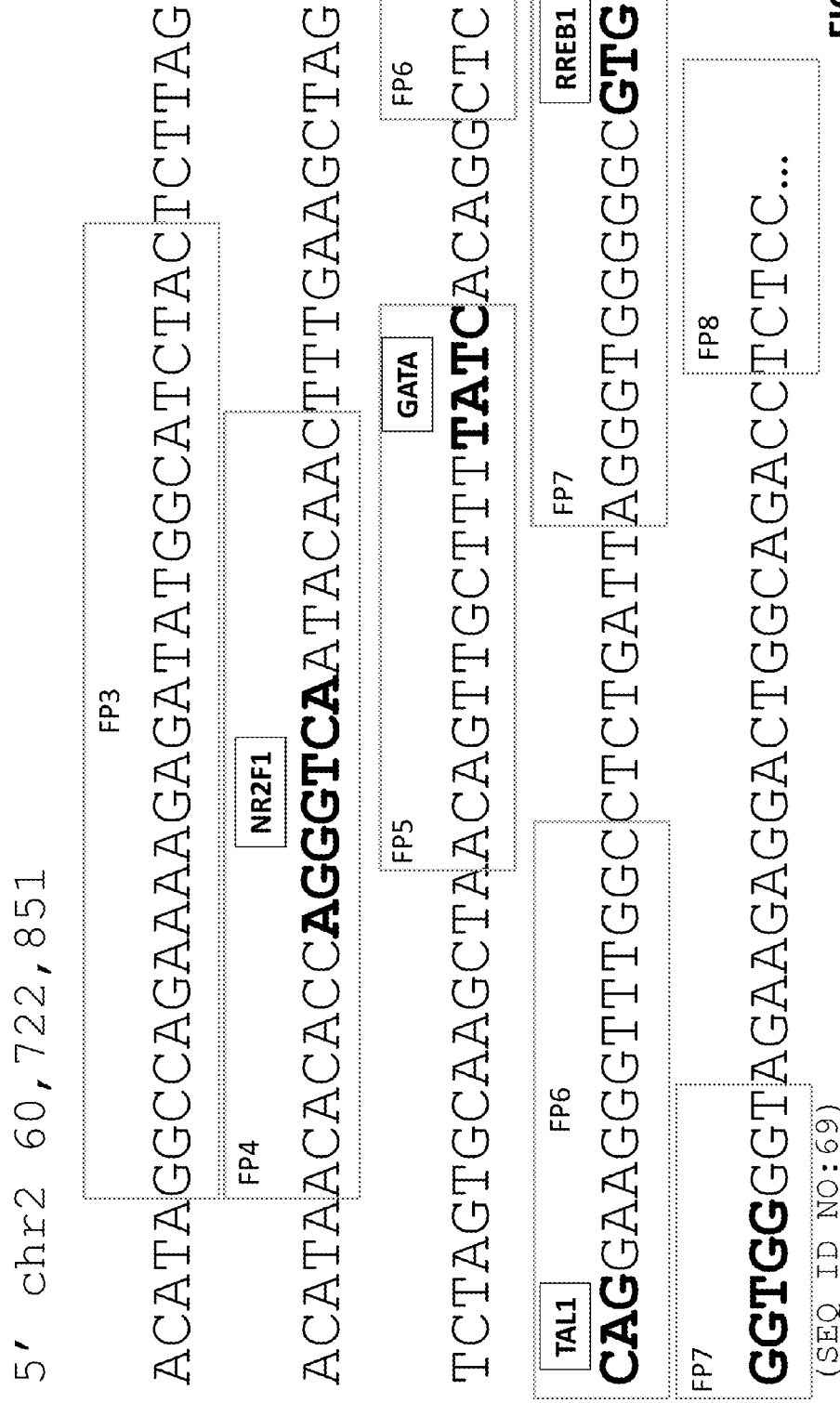

In addition, the sequence of the region was scanned for potential TF binding motifs and several were identified (see FIG. 1), the footprinted regions. Furthermore, we found increased rates of editing in both the upstream and downstream flanking sequences, indicating the presence of additional binding sites. The presence of additional factors is supported in the DNase I footprint itself in addition to the clear conservation of its underlying sequence elements (footprint 5). As described herein, the vast majority of genome editing events found in low γ-globin-expressing cells created alleles that did not ablate a functional GATA1 binding site.

Example 3

TALEN Cleavage Pairs for the +58 Region

TALEN pairs were made and used to probe the footprint regions for an alteration in fetal globin expression via a knockdown of BCL11A. FIG. 2 shows a schematic depicting the cleavage sites of the TALENs relative to the observed footprints and the putative transcription factor binding motifs. The TALENs used are shown below in Table 2 (see also U.S. Patent Publication No. 20150132269).

TABLE 2

TALENs used in the +58 enhancer footprint analysis

| Sample (T pair) | SBS # | target 5'→3' | # of RVDs | SEQ ID NO: | N → C RVD Sequence | Footprint |
|---|---|---|---|---|---|---|
| 1 | 102830 | gtGTGCATAAGTAAGAGCAga | 17 | 12 | NN-NG-NN-HD-NI-NG-NI-NI-NN-NG-NI-NI-NN-NI-NN-HD-NI | FP1 |
|   | 102831 | ctGTATGGACTTTGCACTGga | 17 | 13 | NN-NG-NI-NG-NN-NN-NI-HD-NG-NG-NG-NN-HD-NI-HD-NG-NK |   |
| 2 | 102832 | gtAAGAGCAGATAGCTGATtc | 17 | 14 | NI-NI-NN-NI-NN-HD-NI-NN-NI-NG-NI-NN-HD-NG-NN-NI-NG | FP2 |
|   | 102833 | atGTTATTACCTGTATGGAct | 17 | 15 | NN-NG-NG-NI-NG-NG-NI-HD-HD-NG-NN-NG-NI-NG-NN-NN-NI |   |
| 3 | 102834 | atAGCTGATTCCAGTGCAAag | 17 | 16 | NI-NN-HD-NG-NN-NI-NG-NG-HD-HD-NI-NN-NG-NN-HD-NI-NI | FP2 |
|   | 102835 | ttTTCTGGCCTATGTTATTac | 17 | 17 | NG-NG-HD-NG-NN-NN-HD-HD-NG-NI-NG-NN-NG-NG-NI-NG-NG |   |
| 4 | 102836 | gtGCAAAGTCCATACAGGTaa | 17 | 18 | NN-HD-NI-NI-NI-NN-NG-HD-HD-NI-NG-NI-HD-NI-NN-NN-NG | Between FP2 and FP3 |
|   | 102837 | atGCCATATCTCTTTTCTGgc | 17 | 19 | NN-HD-HD-NI-NG-NI-HD-NG-HD-NG-NG-NG-NG-HD-NG-NK |   |
| 5 | 102838 | atACAGGTAATAACATAGGcc | 17 | 20 | NI-HD-NI-NN-NN-NG-NI-NI-NG-NI-NI-HD-NI-NG-NI-NN-NK | FP3 |
|   | 102839 | ctAAGAGTAGATGCCATATct | 17 | 21 | NI-NI-NN-NI-NN-NG-NI-NN-NI-NG-NN-HD-HD-NI-NG-NI-NG |   |
| 6 | 102840 | atAACATAGGCCAGAAAAGag | 17 | 22 | NI-NI-HD-NI-NG-NI-NN-NN-HD-HD-NI-NN-NI-NI-NI-NI-NK | FP3 |

TABLE 2-continued

TALENs used in the +58 enhancer footprint analysis

| Sample (T pair) | SBS # | target 5'→3' | # of RVDs | SEQ ID NO: | N → C RVD Sequence | Footprint |
|---|---|---|---|---|---|---|
|  | 102841 | gtGTTATGTCTAAGAGTAGat | 17 | 23 | NN-NG-NG-NI-NG-NN-HD-NG-NI-NI-NN-NI-NN-NG-NI-NK |  |
| 7 | 102842 | ctCTTAGACATAACACACCag | 17 | 24 | HD-NG-NG-NI-NN-NI-HD-NI-NG-NI-NI-HD-NI-HD-NI-HD-HD | FP4 |
|  | 102843 | ctAGACTAGCTTCAAAGTTgt | 17 | 25 | NI-NN-NI-HD-NG-NI-NN-HD-NG-NG-HD-NI-NI-NI-NN-NG-NG |  |
| 8 | 102844 | atAACACACCAGGGTCAATac | 17 | 26 | NI-NI-HD-NI-HD-NI-HD-HD-NI-NN-NN-NN-NG-HD-NI-NI-NG | FP4 |
|  | 102845 | gtTAGCTTGCACTAGACTAgc | 17 | 27 | NG-NI-NN-HD-NG-NG-NN-HD-NI-HD-NG-NI-NN-HD-NG-NI |  |
| 9 | 102846 | gtCAATACAACTTTGAAGCta | 17 | 28 | HD-NI-NI-NG-NI-HD-NI-NI-HD-NG-NG-NG-NN-NI-NI-NN-HD | Between FP4 and FP5 |
|  | 102847 | atAAAAGCAACTGTTAGCtt | 17 | 29 | NI-NI-NI-NI-NN-HD-NI-NI-HD-NG-NN-NG-NG-NI-NN-HD |  |
| 10 | 102848 | ttGAAGCTAGTCTAGTGCAag | 17 | 30 | NN-NI-NI-NN-HD-NG-NI-NN-NG-HD-NG-NI-NN-NG-NN-HD-NI | FP5 |
|  | 102849 | ctGGAGCCTGTGATAAAAGca | 17 | 31 | NN-NN-NI-NN-HD-HD-NG-NN-NG-NN-NI-NG-NI-NI-NI-NI-NK |  |
| 11 | 102850 | ctAGTCTAGTGCAAGCTAac | 17 | 32 | NI-NN-NG-HD-NG-NI-NN-NG-NN-HD-NI-NI-NN-HD-NG-NI | FP5 |
|  | 102851 | ctTCCTGGAGCCTGTGATAaa | 17 | 33 | NG-HD-HD-NG-NN-NN-NI-NN-HD-HD-NG-NN-NG-NN-NI-NG-NI |  |
| 12 | 102852 | gtGCAAGCTAACAGTTGCTtt | 17 | 34 | NN-HD-NI-NI-NN-HD-NG-NI-NI-HD-NI-NN-NG-NG-NN-HD-NG | FP5 |
|  | 102853 | atCAGAGGCCAAACCCTTCct | 17 | 35 | HD-NI-NN-NI-NN-NN-HD-HD-NI-NI-NI-HD-HD-HD-NG-NG-HD |  |
| 13 | 102854 | ctAACAGTTGCTTTTATCAca | 17 | 36 | NI-NI-HD-NI-NN-NG-NG-NN-HD-NG-NG-NG-NG-NI-NG-HD-NI | FP6 |
|  | 102855 | ctAATCAGAGGCCAAACCCtt | 17 | 37 | NI-NI-NG-HD-NI-NN-NI-NN-NN-HD-HD-NI-NI-NI-HD-HD-HD |  |
| 14 | 102856 | atCACAGGCTCCAGGAAGGgt | 17 | 38 | HD-NI-HD-NI-NN-NN-HD-NG-HD-HD-NI-NN-NN-NI-NI-NN-NK | FP6 |
|  | 102857 | ctACCCCACCCACGCCCCac | 17 | 39 | NI-HD-HD-HD-HD-NI-HD-HD-HD-NI-HD-NN-HD-HD-HD-HD-HD |  |
| 15 | 102858 | ctCCAGGAAGGGTTTGGCCtc | 17 | 40 | HD-HD-NI-NN-NN-NI-NI-NN-NN-NN-NG-NG-NG-NN-NN-HD-HD | FP7 |
|  | 102859 | ctACCCCACCCACGCCCCac | 17 | 41 | NI-HD-HD-HD-HD-NI-HD-HD-NI-HD-NN-HD-HD-HD-HD-HD |  |
| 16 | 102860 | ttGGCCTCTGATTAGGGTGgg | 17 | 42 | NN-NN-HD-HD-NG-HD-NG-NN-NI-NG-NG-NI-NN-NN-NN-NG-NK | FP7 |
|  | 102861 | ctGCCAGTCCTCTTCTACCcc | 17 | 43 | NN-HD-HD-NI-NN-NG-HD-HD-NG-HD-NG-NG-HD-NG-NI-HD-HD |  |

TABLE 2-continued

TALENs used in the +58 enhancer footprint analysis

| Sample (T pair) | SBS # | target 5'→3' | # of RVDs | SEQ ID NO: | N → C RVD Sequence | Footprint |
|---|---|---|---|---|---|---|
| 17 | 102862 | atTAGGGTGGGGCGTGGGtg | 17 | 44 | NG-NI-NN-NN-NN-NG-NN-NN-NN-NN-NN-NN-NG-NN-NN-NG-NN-NK | FP7 |
|  | 102863 | atGGAGAGGTCTGCCAGTCct | 17 | 45 | NN-NN-NI-NN-NI-NN-NN-NG-HD-NG-NN-HD-HD-NI-NN-NG-HD |  |
| 18 | 102864 | gtGGGGTAGAAGAGGACTGgc | 17 | 46 | NN-NN-NN-NN-NG-NI-NN-NI-NI-NN-NI-NN-NN-NI-HD-NG-NK | FP8 |
|  | 102865 | ctGGGCAAACGGCCACCGAtg | 17 | 47 | NN-NN-NN-HD-NI-NI-NI-HD-NN-NN-HD-HD-NI-HD-HD-NN-NI |  |
| 19 | 102866 | ctGGCAGACCTCTCCATCGgt | 17 | 48 | NN-NN-HD-NI-NN-NI-HD-HD-NG-HD-NG-HD-HD-NI-NG-HD-NK | FP8 |
|  | 102867 | ctTCCGAAAGAGGCCCCCtg | 17 | 49 | NG-HD-HD-NN-NI-NI-NN-NI-NN-NN-HD-HD-HD-HD-HD-HD-HD |  |
| 20 | 102868 | atCGGTGGCCGTTTGCCCag | 16 | 50 | HD-NN-NN-NG-NN-NN-HD-HD-NN-NG-NG-NG-HD | FP8 |
|  | 102869 | atCACCAAGAGAGCCTTCCga | 17 | 51 | HD-NI-HD-HD-NI-NI-NN-NI-NN-NI-NN-HD-HD-NG-NG-HD-HD |  |
| 21 | 102870 | gtTTGCCCAGGGGGGCCTCtt | 17 | 52 | NG-NG-NN-HD-HD-HD-NI-NN-NN-NN-NN-NN-NN-HD-HD-NG-HD | FP8 |
|  | 102871 | atTCTCCATCACCAAGAGAgc | 17 | 53 | NG-HD-NG-HD-HD-NI-NG-HD-NI-HD-HD-NI-NI-NN-NI-NN-NI |  |
| 22 | 102872 | ttGCCCAGGGGGCCTCTTtc | 17 | 54 | NN-HD-HD-HD-NI-NN-NN-NN-NN-NN-NN-HD-HD-NG-HD-NG-NG | FP8 |
|  | 102873 | atAAAATCCAATTCTCCATca | 17 | 55 | NI-NI-NI-NI-NG-HD-HD-NI-NI-NG-NG-HD-NG-HD-HD-NI-NG |  |
| 23 | 102874 | ctTTCGGAAGGCTCTCTTGgt | 17 | 56 | NG-NG-HD-NN-NN-NI-NI-NN-NN-HD-NG-HD-NG-HD-NG-NG-NK | Distal to FP8 |
|  | 102875 | atTGAGAAATAAAATCCAAtt | 17 | 57 | NG-NN-NI-NN-NI-NI-NI-NG-NI-NI-NI-NI-NG-HD-NI-NI |  |
| 24 | 103049 | atACAGGGCTGGCTCTATGcc | 17 | 58 | NN-HD-NI-NN-NN-NN-HD-NG-NN-NN-HD-NG-HD-NG-NI-NG-NK | FP1 |
|  | 103050 | ctATCTGCTCTTACTTATgc | 16 | 59 | NI-NG-HD-NG-NN-HD-NG-HD-NG-NG-NI-HD-NG-NG-NI-NG |  |
| 25 | 103051 | gtAATAACATAGGCCAGAAaa | 17 | 60 | NI-NI-NG-NI-NI-HD-NI-NG-NI-NN-NN-HD-HD-NI-NN-NI-NI | FP3 |
|  | 103052 | gtTATGTCTAAGAGTAGATgc | 17 | 61 | NG-NI-NG-NN-NG-HD-NG-NI-NI-NN-NI-NN-NG-NI-NN-NG |  |
| 26 | 103053 | atAGGCCAGAAAAGAGATAtg | 17 | 62 | NI-NN-NN-HD-HD-NI-NN-NI-NI-NI-NI-NN-NI-NN-NI-NG-NI | FP3 |
|  | 103054 | ctGGTGTGTTATGTCTAAGag | 17 | 63 | NN-NN-NG-NN-NN-NG-NG-NI-NG-NN-NG-HD-NG-NI-NI-NK |  |
| 27 | 103055 | atAGGCCAGAAAAGAGATAtg | 17 | 64 | NI-NN-NN-HD-HD-NI-NN-NI-NI-NI-NI-NN-NI-NN-NI-NG-NI | FP3 |

TABLE 2-continued

TALENs used in the +58 enhancer footprint analysis

| Sample (T pair) | SBS # | target 5'→3' | # of RVDs | SEQ ID NO: | N → C RVD Sequence | Footprint |
|---|---|---|---|---|---|---|
| | 103056 | atTGACCCTGGTGTGTTATgt | 17 | 65 | NG-NN-NI-HD-HD-HD-NG-NN-NN-NG-NN-NG-NN-NG-NG-NI-NG | |

Nucleases were first assessed for editing efficiency by transient transfection of expression constructs into K562 cells followed by genotyping of the target locus using the Surveyor/Cell endonuclease. ORFs for maximally active nucleases against each genomic position were re-cloned into an expression vector optimized for mRNA production bearing a 5' and 3' UTRs and a synthetic polyA signal. The mRNAs were generated using the mMessage mMachine T7 Ultra kit (Ambion) following the manufacturer's instructions. In vitro synthesis of nuclease mRNAs used either a pVAX-based vector containing a T7 promoter, the nuclease proper and a polyA motif for enzymatic addition of a polyA tail following the in vitro transcription reaction, or a pGEM based vector containing a T7 promoter, a 5'UTR, the nuclease proper, a 3'UTR and a 64 bp polyA stretch.

All TALENs were used to cleave the BCL11A+58 enhancer region in CD34 cells and transfected cells were analyzed for relative gamma expression after erythrocyte differentiation. Briefly, human CD34+ cells were purchased from AllCells. For small-scale mRNA transfections we used a BTX device (Harvard Apparatus), using the CD34+ cell program per manufacturer's instructions. Per transfection we typically used 2 ug of mRNA for each ZFN or 4 ug of mRNA for each TALEN and 200,000 cells in a 100 ul volume. Large-scale transfections using the MaxCyte device were performed according to manufacturer's instructions. Per transfection we typically used 3 million cells, a total volume of 100 ul and 8ug of each nuclease mRNA. After transfection, the cells were exposed to transient hypothermia19 for 16 hours and then cultured at 37° C.

Following electroporation the cells were treated as follows. Day 0 to day 7:4×104/mL CD34+ cells were cultured in EDM [EDM: IMDM, human holo-transferrin (330 µg/ml); insulin (10 µg/ml); heparin (2 IU/ml), 5% plasma] in the presence of 10-6 M hydrocortisone, 100 ng/mL SCF, 5 ng/mL IL-3, and 3 IU/mL Epo. On day 4, 1 volume of cell culture was diluted in 4 volumes of fresh medium containing SCF, Epo, and hydrocortisone. Day 7 to day 11: the cells were resuspended at 4×105/mL in EDM supplemented with SCF and Epo. Day 11 to day 15 and out to day 20: the cells are cultured in EDM supplemented with Epo alone. Cell counts are adjusted to between 7.5×105 to 1×106 on day 11 and harvested on day 13-14 for mRNA analysis and day 20 for immunofluorescent staining of γ-globin and fluorescence-activated cell sorting.

To assess the amount of expression from the globin locus, whole-cell RNA was isolated from in vitro generated erythrocytes using a High Pure RNA Isolation Kit (Roche). The levels of mRNA for the individual globin genes (α, β, and γ) were then measured by real-time RT-qPCR on an ABI 7300 RT-PCR machine mode using the following manufacturer-provided probesets: α-globin (HBA), Hs00361191_g1; β-globin (HBB), Hs00758889_s1; γ-globin (HBG), Hs00361131_g1; 18S rRNA (18S) Hs99999901_s1.

Figure 3:
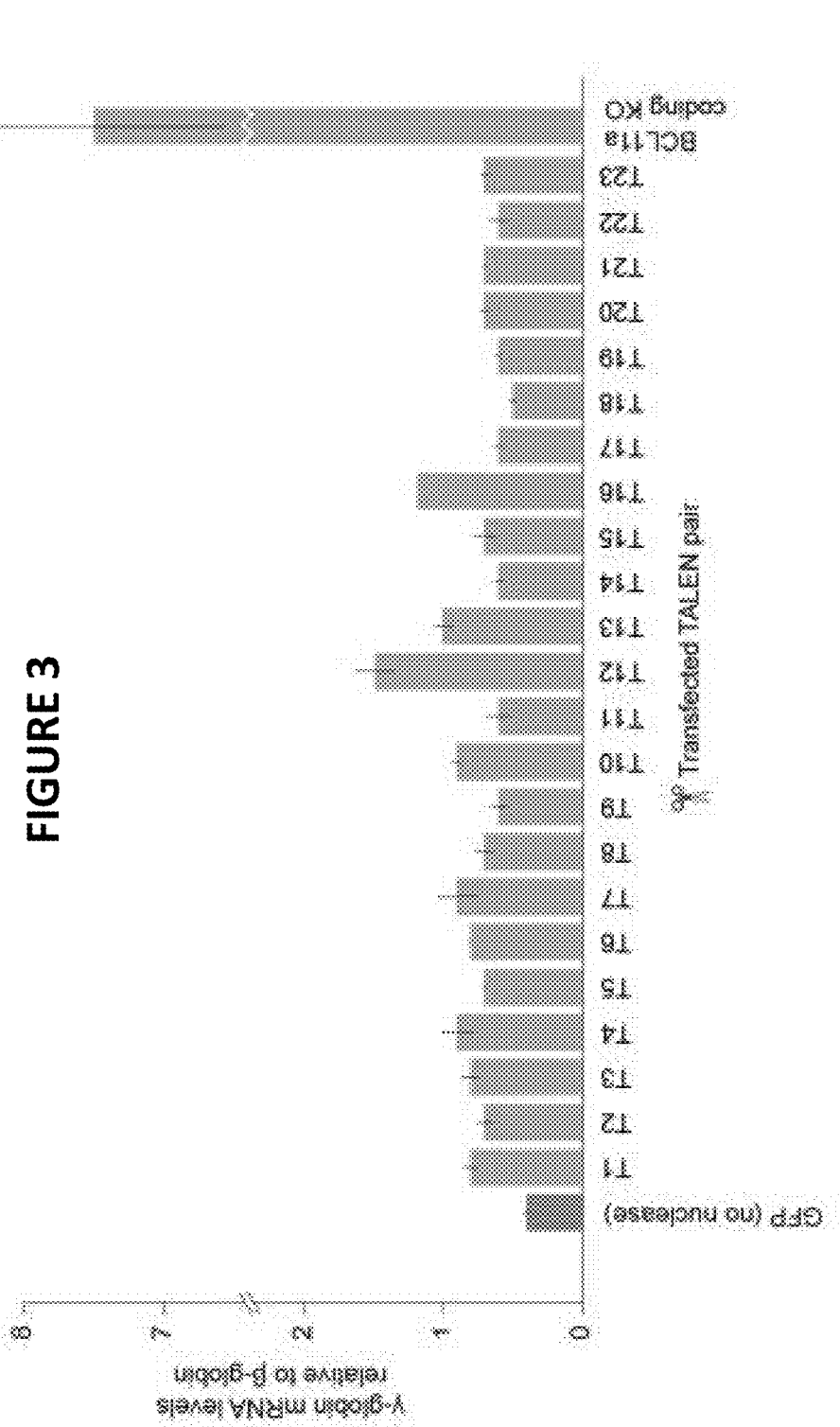
FIG. 3 is a graph depicting the expression of human gamma globin (HBG) as a relative ratio of HBG to human beta globin (HBB) following erythroid differentiation of edited HSPC CD34+ cells shown. The data indicates that cleavage with the TALEN pairs 12, 13 and 16 resulted in increased gamma globin expression.
Figure 4A:
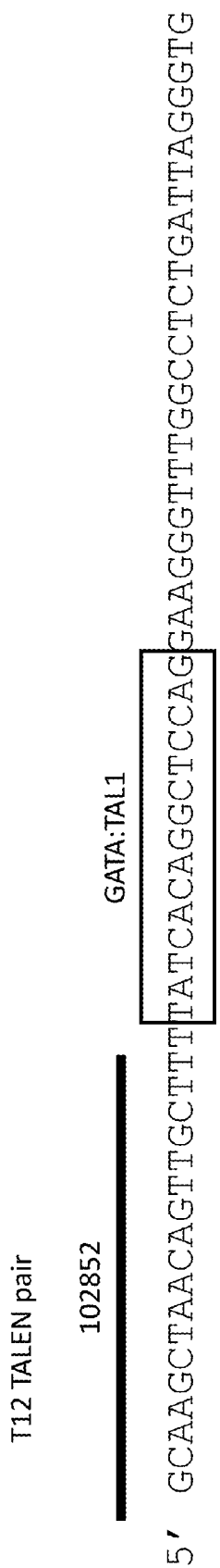
FIGS. 4A through 4C depict the location of the TALEN target sites relative to the transcription factor binding motifs.
Figure 4B:
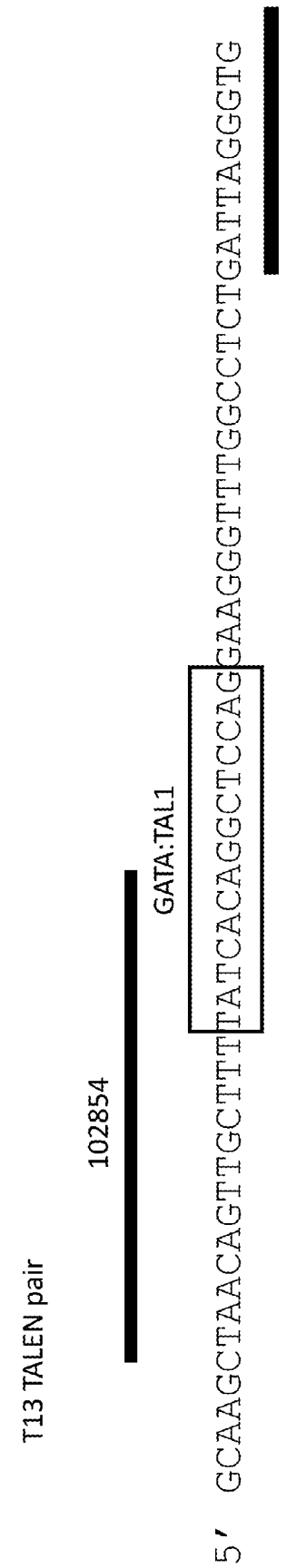
Figure 4C:
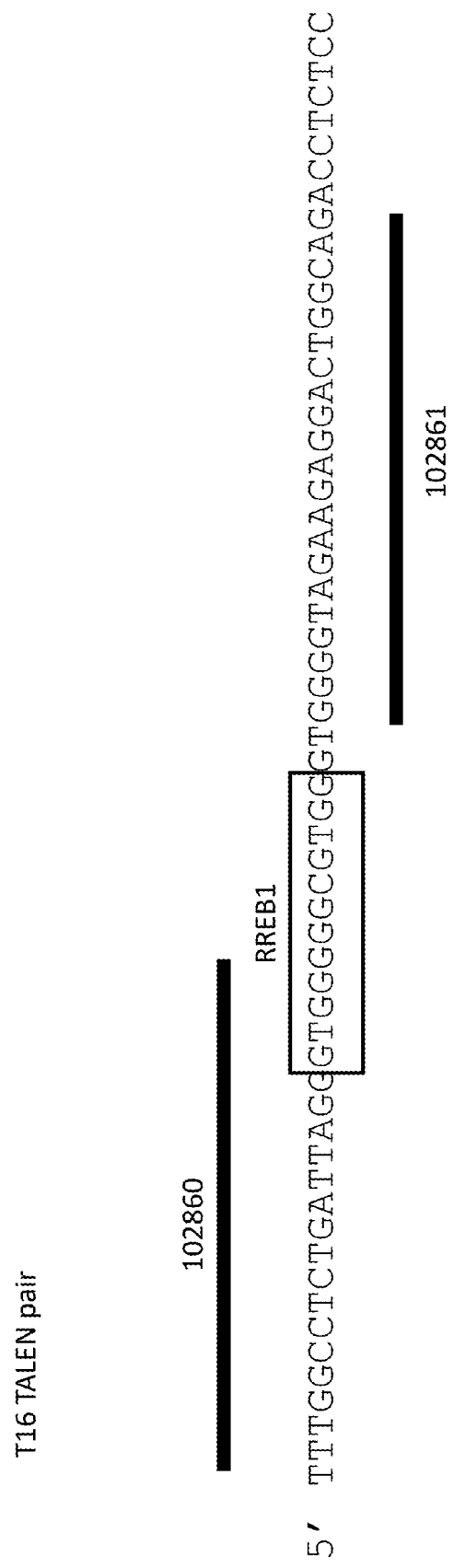

Exemplary data (FIG. 3) demonstrate that cleavage at specific sites in the +58 region cause an increase in the expression of gamma globin relative to beta globin expression. Furthermore, successful upregulation of gamma globin expression appears to be linked to cleavage at the GATA1:TAL1 binding motif (FIGS. 4A and 4B) and the RREB1 binding motif (FIG. 4C).

Example 4

Use of RNA Guided Nucleases to Cleave the BCL11A+58 Enhancer Region

To achieve similar results using an RNA guided CRISPR/Cas system, guide RNAs for use with S. pyogenes Cas9 were designed. For cleaving at or near the GATA1:TAL1 subsite, the following guide RNA corresponding to this DNA sequence was designed:

(i)
                                                            (SEQ ID NO: 74)
5' TTGCTTTTATCACAGGCTCC.

To cleave the enhancer at or near the RREB1 binding motif, the following guide RNAs corresponding to these DNA sequences were designed:

(i)
                                                             (SEQ ID NO: 75)
5' ATTAGGGTGGGGCGTGGGT (ii)
                                                             (SEQ ID NO: 76)
5' TTAGGGTGGGGCGTGGGTG (iii)
                                                             (SEQ ID NO: 77)
5' TCTGATTAGGGTGGGGCGT.

To determine if cleavage with a CRISPR/Cas system comprising one or more of these guide RNAs could cause an increase in gamma globin expression, CD34+ HSPCs are transfected with a varying amount of Cas9 nuclease mRNA as described above along with a constant amount of a plasmid designed to express the guide RNAs to target the Cas9 nuclease activity to the +58 enhancer locus. Following cleavage with the CRIPSR/Cas system, the CD34+ HSPC are differentiated into erythrocytes as described above and gamma globin expression as measured as above. The results show that the guide RNAs are active in the CRISPR/Cas system and that gamma globin expression is increased.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. An isolated genetically modified cell comprising a genomic modification at one cleavage site made by a zinc finger nuclease, (ZFN) or TAL-effector domain nuclease (TALEN), which ZFN or TALEN binds to a target site as shown in any of SEQ ID Nos:58-62, 65 or 74-77, wherein the genomic modification comprises insertions and/or deletions within the one cleavage site.

2. The genetically modified cell of claim 1, wherein the cell is a stem cell.

3. The genetically modified cell of claim 2, wherein the stem cell is a hematopoietic stem cell.

4. The genetically modified cell of claim 3, wherein the hematopoietic stem cell is a CD34+ cell.

5. A genetically modified differentiated cell descended from the stem cell of claim 2.

6. The genetically modified cell of claim 5, wherein the cell is a red blood cell (RBC).

7. The genetically modified cell of claim 1, wherein the nuclease is introduced into the cell as a polynucleotide.

8. The genetically modified cell of claim 1, wherein the insertion comprises integration of a donor polynucleotide encoding a transgene.

9. A pharmaceutical composition comprising the genetically modified cell of claim 1.

10. A DNA binding molecule comprising a TALE-effector protein (TALE) or a single guide RNA that binds to a target site as shown in any of SEQ ID Nos:58-62, 65 or 74-77.

11. A polynucleotide encoding one or more DNA-binding molecule of claim 10.

12. An isolated cell comprising one or more DNA-binding molecules according to claim 10.

13. A kit comprising a polynucleotide according to claim 11.

* * * * *